US011179258B2

United States Patent
Shimada et al.

(10) Patent No.: US 11,179,258 B2
(45) Date of Patent: Nov. 23, 2021

(54) LIMB MOTION SUPPORT DEVICE

(71) Applicant: HONDA MOTOR CO., LTD., Tokyo (JP)

(72) Inventors: Kei Shimada, Saitama (JP); Toru Takenaka, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 586 days.

(21) Appl. No.: 15/934,048

(22) Filed: Mar. 23, 2018

(65) Prior Publication Data

US 2018/0280178 A1 Oct. 4, 2018

(30) Foreign Application Priority Data

Mar. 28, 2017 (JP) .............................. JP2017-063942

(51) Int. Cl.
*A61F 5/01* (2006.01)
*A61H 1/02* (2006.01)
(Continued)

(52) U.S. Cl.
CPC ......... *A61F 5/0102* (2013.01); *A61H 1/0237* (2013.01); *A61H 3/00* (2013.01);
(Continued)

(58) Field of Classification Search
CPC ............ A61F 5/0102; A61F 2005/0155; A61F 2005/0158; A61F 2005/0151; A61F 2005/0153; A61F 2005/0169; A61F 2005/0179; A61F 2005/0197; A61F 2005/0211; A61F 2005/0248; A61F 5/01; A61F 5/0104; A61F 5/0106;
(Continued)

(56) References Cited

U.S. PATENT DOCUMENTS

2006/0241539 A1* 10/2006 Agrawal
2016/0184166 A1* 6/2016 Takenaka .................. A61F 2/60
623/27
2018/0177667 A1* 6/2018 Uemura

FOREIGN PATENT DOCUMENTS

JP 3032086 2/2000
JP 2010-110543 5/2010
(Continued)

OTHER PUBLICATIONS

German Office Action dated Aug. 20, 2020, English translation included, 31 pages.

(Continued)

*Primary Examiner* — Camtu T Nguyen
(74) *Attorney, Agent, or Firm* — Rankin, Hill & Clark LLP

(57) ABSTRACT

Provided is a motion transmission mechanism 30 of a limb motion support device 1A configured so as not to transmit the movements of a pair of braces 10R and 10L attached to right and left legs to spring members 20R and 20L in a state where the bending degrees of the right and left legs are smaller than a predetermined bending degree in the case where both of the right and left legs equipped with the braces 10L and 10R are bent from a stretched state and configured to transmit the movements of the braces 10L and 10R to the spring members 20L and 20R via a wire 31 after the bending degrees of the legs increase to be larger than the predetermined bending degree.

12 Claims, 16 Drawing Sheets

(51) Int. Cl.
*A61H 3/00* (2006.01)
*B25J 9/10* (2006.01)
*B25J 9/00* (2006.01)

(52) U.S. Cl.
CPC ........... *B25J 9/0006* (2013.01); *B25J 9/1045* (2013.01); *A61F 2005/0155* (2013.01); *A61F 2005/0158* (2013.01); *A61H 2201/164* (2013.01); *A61H 2201/165* (2013.01); *A61H 2201/1642* (2013.01); *A61H 2205/10* (2013.01)

(58) Field of Classification Search
CPC .. A61H 1/0237; A61H 3/00; A61H 2201/164; A61H 2201/1642; A61H 2201/165; A61H 2205/10; A61H 1/024; A61H 1/0244; A61H 1/0255; A61H 1/0262; A61H 2001/0211; A61H 2001/0248; A61H 2003/001–007; B25J 9/0006; B25J 9/1045; B25J 9/10; B25J 9/106

USPC ..................................................... 601/33–35
See application file for complete search history.

(56) References Cited

FOREIGN PATENT DOCUMENTS

| | | |
|---|---|---|
| JP | 2010-142353 | 7/2010 |
| JP | 2011-217825 | 11/2011 |
| JP | 2015-163180 | 9/2015 |
| JP | 2016-182666 | 10/2016 |
| WO | 2016/006432 A1 | 1/2016 |
| WO | 2016/104330 A1 | 6/2016 |

OTHER PUBLICATIONS

Japanese Office Action dated Aug. 18, 2020, 3 pages.
Chinese Office Action dated Dec. 23, 2019, 7 pages.

* cited by examiner

BOTH LEGS: BENT

LIMB MOTION SUPPORT DEVICE

BACKGROUND OF THE INVENTION

Field of the Invention

The present invention relates to a device which supports a bending and stretching motion of the right and left limbs such as human legs.

Description of the Related Art

Conventionally, a wide variety of devices for supporting the motions of an aged person or the like have been proposed. For example, Japanese Patent Application Laid-Open No. 2015-163180 (hereinafter, referred to as Patent Document 1) proposes a device which supports a user in a bending-forward motion of his/her upper body so as to reduce the burden on the user during bending his/her upper body forward. Moreover, Japanese Patent No. 3032086 (hereinafter, referred to as Patent Document 2) and Japanese Patent Application Laid-Open No. 2016-182666 (hereinafter, referred to as Patent Document 2) propose devices which support a walking motion of a user.

As a motion which an aged person or the like easily feels burdened, for example, there is a standing-up motion by stretching his/her legs from a state of relatively deep bends of the legs such as a state of sitting in a chair or the like or a state of squatting.

In the device which supports this type of motions, to enable a user to smoothly start to bend both legs from the standing state, it is desirable that an assisting force inhibiting the user from bending the legs does not act in a state where the bending degrees of both legs are relatively small, while an assisting force that assists the user in stretching the legs acts in a state where the legs are sufficiently bent.

The devices in Patent Documents 1 and 2, however, are not able to perform the aforementioned motion support. Moreover, a device provided with an actuator such as an electric motor for generating an assisting force, as in Patent Document 3, is able to perform a motion support as described above by controlling the actuator. However, it requires a power supply unit or the like in addition to the actuator, and therefore the device configuration tends to be complicated and heavy.

Therefore, the device as in Patent Document 3 tends to be a nuisance for a user and tends to increase the burden on the user in walking or the like on the contrary or to cause the user to feel uncomfortable disadvantageously.

The present invention has been made in view of the above background. Therefore, it is an object of the present invention to provide a limb motion support device capable of generating an assisting force for appropriately supporting a user in a bending and stretching motion of the right and left limbs such as user's legs, with a simple configuration not requiring an actuator or a configuration requiring only a small actuator.

SUMMARY OF THE INVENTION

According to an aspect of the present invention, there is provided a limb motion support device including: a pair of braces adapted to be attached to the right and left limbs of a user, respectively; one or more spring members that generate elastic forces for assisting in a bending and stretching motion of the right and left limbs by an elastic deformation, and are shared between the right and left limbs; and a motion transmission mechanism that transmits a motion between the pair of braces and the spring member so as to elastically deform the spring member by transmitting movements of the pair of braces associated with the bending and stretching motion of the right and left limbs to the spring member, wherein the motion transmission mechanism is configured not to transmit the movements of the pair of braces to the spring member in a state where the bending degrees of the right and left limbs are smaller than a predetermined first bending degree, in a case where both of the right and left limbs equipped with the pair of braces are bent from a stretched state, but configured to transmit the movements of the pair of braces to the spring member after increasing the bending degrees of the right and left limbs to a bending degree larger than the first bending degree (First invention).

In the present invention, the term "bending degrees" of the right and left limbs means, more specifically, bending degrees at joints (knee joints or elbow joints) in the respective middle parts of the right and left limbs, bending degrees (bending degrees relative to the user's body) at joints (hip joints or shoulder joints) at the root ends of the right and left limbs, or the total bending degrees, each of which are obtained by adding up the bending degree at the joint in the middle part of each of the right and left limbs to the bending degree at the joint at each of the root ends of the right and left limbs.

According to the first invention, the motion transmission mechanism is configured as described above. Therefore, the motion transmission mechanism does not transmit the movements of the pair of braces to the spring member in a state where the bending degrees of the right and left limbs are smaller than a predetermined first bending degree, thereby preventing the elastic force of the spring member from being generated. This avoids an assisting force generated by the elastic force of the spring member from acting on the user.

Moreover, if the bending degrees of the right and left limbs increase to bending degrees larger than the first bending degree, the movements of the pair of braces are transmitted to the spring member, thereby enabling a generation of an elastic force appropriate to the bending degrees of the right and left limbs. This enables the assisting force generated by the elastic force of the spring member to act on the user.

In this case, the motion transmission mechanism is intended to transmit the movements of the pair of braces associated with the bending and stretching of the right and left limbs to the spring member, and therefore the motion transmission mechanism is able to be implemented without the need for an actuator.

Therefore, according to the first invention, it is possible to generate an assisting force for appropriately supporting a bending and stretching motion of the right and left limbs such as user's legs or the like with a simple configuration without the need for an actuator. Moreover, there is no need to use a power supply or the like for use in operating an actuator, and therefore the motion support device is able to be lightweight.

In the above first invention, the right and left limbs may be the right and left legs of the user. In this case, preferably, in a case where one of the right and left legs equipped with the pair of braces is stretched and the other leg is bent, the motion transmission mechanism is configured not to transmit the movements of the pair of braces to the spring member in a state where a bending degree of the other leg is smaller than a predetermined second bending degree, which is larger than the first bending degree (Second invention).

According thereto, the elastic force of the spring member is not generated or is prevented from being generated as much as possible.

In the above first or second invention, the following embodiment may be employed: the limb motion support device includes a pair of the spring members and a flexible long member as a constituent element of the motion transmission mechanism, the flexible long member is disposed to be engaged with the pair of braces in such a way that at least a part of the flexible long member runs due to a change in a path length of the flexible long member in at least a part of a section between both ends of the flexible long member according to a change in the bending degrees of the right and left limbs, and one end of each of the pair of spring members is connected to both ends of the flexible long member, and the motion transmission mechanism is configured to run at least a part of the flexible long member according to a change in the bending degrees of the right and left limbs so as to prevent an occurrence of tensions, which cause an elastic deformation of the pair of spring members, in the flexible long member in a state where the bending degrees of the right and left limbs are smaller than the first bending degree, and configured to cause an elastic deformation of the pair of spring members by running both ends of the flexible long member so as to apply a pulling force or a compressive force to the pair of spring members from the flexible long member according to an increase in the bending degrees of the right and left limbs with the other end of each of the pair of spring members bound to an external first member of each of the pair of spring members in a state where the bending degrees of the right and left limbs are larger than the first bending degree (Third invention).

According thereto, in the case where the bending degrees of the right and left limbs are larger than the first bending degree, the movements of the pair of braces associated with an increase in the bending degrees of the right and left limbs are transmitted to both of the pair of spring members via the flexible long member, thereby enabling both of the pair of spring members to generate elastic forces. Consequently, assisting forces are able to be applied to the user.

Moreover, a change in the path length of the flexible long member in at least a part of the section between both ends of the flexible long member according to a change in the bending degrees of the right and left limbs is able to be easily achieved by setting the disposition pattern of the flexible long member, setting the length of the flexible long member, or the like. Therefore, the movements of the pair of braces caused by the bending motions of the right and left limbs are able to be absorbed by a change in the path length. Thereby, in the state where the bending degrees of the right and left limbs are smaller than the first bending degree, it is possible to easily prevent an occurrence of a tension, which causes an elastic deformation of the pair of spring members, in the flexible long member without the need for a clutch mechanism or the like.

Furthermore, the flexible long member is able to be formed of a wire or the like, thereby easily enabling a reduction in size or weight of the limb motion support device.

In the above third invention, the following embodiment may be employed: the motion transmission mechanism is configured to, in a state where the bending degrees of the right and left limbs are smaller than the first bending degree, run both ends of the flexible long member according to a change in the bending degrees of the right and left limbs so that each of the pair of spring members moves in a direction in which the other end of each of the pair of spring members or a second member connected to the other end comes close to the external first member of each of the pair of spring members with an increase in the bending degrees of the right and left limbs, and configured so that the other end of each of the pair of spring members or the second member connected to the other end engages with the external first member of each of the pair of spring members when the bending degrees of the right and left limbs increase up to the bending degree equal to or higher than the first bending degree, by which the other end of each of the pair of spring members is bound to each of the first members (Fourth invention).

According thereto, in the case where both of the right and left limbs are bent from the stretched state, motion transmission switching from the pair of braces to the pair of spring members (switching from a state where the elastic deformation of the pair of spring members does not occur to a state where the elastic deformation occurs) is able to be smoothly performed with a simple configuration.

In the above first or second invention, the following embodiment may be employed: the limb motion support device includes a pair of the spring members and a flexible long member as a constituent element of the motion transmission mechanism, the flexible long member is disposed to be engaged with the pair of braces in such a way that at least a part of the flexible long member runs due to a change in a path length of the flexible long member in at least a part of the section between both ends of the flexible long member according to a change in the bending degrees of the right and left limbs, and the motion transmission mechanism is configured to run at least a part of the flexible long member according to a change in the bending degrees of the right and left limbs so that a running motion of the flexible long member is not transmitted to the pair of spring members, in a state where the bending degrees of the right and left limbs are lower than the first bending degree, and configured to cause an elastic deformation of the pair of spring members by running both ends of the flexible long member so as to apply a pulling force or a compressive force to the pair of spring members from the flexible long member according to an increase in the bending degrees of the right and left limbs with each of both ends of the flexible long member bound to one end of each of the pair of spring members and with the other end of each of the pair of spring members bound to an external third member of each of the pair of spring members in a state where the bending degrees of the right and left limbs are higher than the first bending degree (Fifth invention).

According thereto, the same advantageous effects as the third invention are achieved.

In the above fifth invention, the following embodiment may be employed: the motion transmission mechanism is configured to, in a state where the bending degrees of the right and left limbs are smaller than the first bending degree, run both ends of the flexible long member according to a change in the bending degrees of the right and left limbs so that each of a pair of fourth members, which are connected to the respective ends of the flexible long member, moves in a direction of coming close to one end of each of the pair of spring members with an increase in the bending degrees of the right and left limbs, with the other end of each of the pair of spring members bound to each of the third members, and configured so that each of the pair of fourth members engages with one end of each of the pair of spring members when the bending degrees of the right and left limbs increase up to the bending degree equal to or higher than the first bending degree, by which each of the ends of the flexible long member is bound to one end of each of the pair of spring members (Sixth invention).

According thereto, similarly to the fourth invention, in the case where both of the right and left limbs are bent from the stretched state, motion transmission switching from the pair of braces to the pair of spring members (switching from a state where the elastic deformation of the spring members does not occur to a state where the elastic deformation occurs) is able to be smoothly performed with a simple configuration.

In the above third or fourth invention, preferably, the flexible long member has a first section in which the path length increases in a case of bending the right limb from a stretched state with the left limb of the right and left limbs stretched, and a second section in which the path length increases in a case of bending the left limb from the stretched state with the right limb of the right and left limbs stretched, and is disposed in such a way that the path length increases in both of the first section and second section in a case where both of the right and left limbs are bent from a state in which both of the right and left limbs are stretched (Seventh invention). This also applies to the above fifth or sixth invention (Eighth invention).

According thereto, in the case where one limb out of the right and left limbs is stretched while the other limb is bent, the bending degree on the upper limit side of the range of the bending degree of the other leg in which the movements of the pair of braces are not transmitted to the spring member is able to be made larger than the first bending degree.

Therefore, particularly in the case where the right and left limbs are the right and left legs of the user, it is possible to prevent the elastic force of the spring member from being generated or to prevent the elastic force from being generated as much as possible.

In the above third, fourth, or seventh invention, if the right and left limbs are right and left legs of the user, preferably the flexible long member is disposed in such a way that the path length increases according to an increase in a bending degree of each leg at a knee of the user (Ninth invention). This also applies to the above fifth, sixth, or eighth invention (10th invention).

According thereto, when both legs of the user are bent at the respective knees, the elastic forces of the spring members are able be generated.

In the above ninth invention, preferably, further the flexible long member is configured in such a way that the path length increases according to an increase in the bending degree of each leg at the knee of the user and an increase in a bending degree of the leg at a hip joint (11th invention). This also applies to the above 10th invention (12th invention).

According thereto, not only when both legs of the user are bent at the respective knees, but also when the legs are bent at the respective hip joints with respect to the body, the elastic forces of the spring members are able to be generated. Moreover, when the user bends the legs at both of the respective knees and hip joints such as when sitting in a chair or the like or squatting, the first bending degree at which the generation of the elastic forces of the spring members is started can be made smaller than the case where the flexible long member is disposed so that the path length is not affected by the bending of the legs at the respective hip joints of the user.

For example, regarding the bending of each leg at the hip joint in walking of the user, one leg is bent at the hip joint thereof while the other leg moves so as to be stretched at the hip joint thereof. Therefore, a change in the path length of the flexible long member, which is caused by the bending of the legs at the hip joints, is counteracted. This enables the prevention of a change in the path length in walking of the user. Consequently, the elastic forces of the spring members are not generated in walking of the user or the generation can be easily prevented.

In the above third, fourth, seventh, ninth, or 11th invention, preferably each of the pair of braces is provided with a circular or eccentric cam-shaped pulley, which rotates in response to the bending of the limb equipped with each brace, and the flexible long member is disposed via the outer periphery of the pulley installed in each of the pair of braces (13th invention). This also applies to the above fifth, sixth, eighth, 10th, or 12th invention (14th invention).

According thereto, it is possible to easily change the path length of the flexible long member in a part of the section according to the bending degrees of the right and left limbs. Moreover, if the pulley is eccentric cam-shaped, the form of the change in the elastic forces of the pair of spring members relative to the bending degrees of the right and left limbs can be set to various forms.

Furthermore, in the third, fourth, seventh, ninth, 11th, or 13 invention, the following embodiment may be employed: each of the pair of braces has at least two link members connected to each other so as to relatively rotate in response to the bending of the limb equipped with the brace and a circular pulley rotatably supported by one of the two link members around the rotation axis in a position offset from the rotation axis of the relative rotation of the two link members; and the flexible long member is disposed via an outer periphery of the pulley of each of the pair of braces (15th invention). This also applies to the above fifth, sixth, eighth, 10th, 12th, or 14th invention (16th invention).

According thereto, each frictional force generated between the pulley and the flexible long member is able to be reduced at the time of bending the right and left limbs. Thereby, an energy loss caused by the friction is able to be reduced.

In the above third, fourth, seventh, ninth, 11th, 13th, or 15th invention, preferably the pair of spring members are installed in the pair of braces, respectively, and the flexible long member is disposed in such a way that a middle part thereof passes through a back side or a front side of a body of the user (17th invention). This also applies to the above fifth, sixth, 8th, 10th, 12th, 14th, or 16th invention (18th invention).

According thereto, the pair of spring members and the flexible long member can be arranged in a compact and well-balanced manner. Furthermore, in the case where the flexible long member is disposed in such a way that the middle part thereof passes through the front side of the body of the user, the limb motion support device according to the present invention is able to be easily attached to the body of the user even if the user is in a sitting position.

Moreover, in the first or second invention, the following embodiment may be employed: a pair of flexible long members are provided as constituent elements of the motion transmission mechanism; one of the pair of flexible long members is disposed to be engaged with the brace adapted to be attached to the left limb in such a way that at least a part of the one of the flexible long member runs due to a change in a path length of the flexible long member at least in a part of a section between both ends of the one flexible long member according to a change in the bending degree of the left limb; the other of the pair of flexible long members is disposed to be engaged with the brace adapted to be attached to the right limb in such a way that at least a part of the other flexible long member runs due to a change in a path length of the flexible long member at least in a part of a section between both ends of the other flexible long member according to a change in the bending degree of the right limb; and the motion transmission mechanism is configured to run at least a part of each of the pair of flexible long members according to a change in the bending degrees of the right and left limbs so that a running motion of each of the flexible long members is not transmitted to the pair of spring members, in a state where the bending degrees of the right and left limbs are lower than the first bending degree, and configured to cause an elastic deformation of the spring member by running at least a part of each of the pair of flexible long members so as to apply a pulling force or a compressive force to the spring member via a pair of fifth members from the pair of flexible long members according to an increase in the bending degrees of the right and left limbs with the pair of fifth members each connected to one end of each of the pair of flexible long members bound to both ends of the spring member in a state where the bending degrees of the right and left limbs are higher than the first bending degree (19th invention).

According thereto, in the case where the bending degrees of the right and left limbs are larger than the first bending degree, the movements of the pair of braces associated with an increase in the bending degrees of the right and left limbs are transmitted to the spring member via each of the pair of flexible long members, thereby enabling the spring member to generate an elastic force. Consequently, an assisting force is able to be applied to the user.

Moreover, a change in the path length of the flexible long member in at least a part of the section between both ends of each of the pair of flexible long members according to a change in the bending degrees of the right and left limbs is able to be easily achieved by setting the disposition pattern of each flexible long member, setting the length of each flexible long member, or the like. Therefore, the movements of the pair of braces caused by the bending motions of the right and left limbs are able to be absorbed by a change in the path length of each flexible long member. Thereby, in the state where the bending degrees of the right and left limbs are smaller than the first bending degree, it is possible to easily prevent an occurrence of a tension, which causes an elastic deformation of the spring member, in each of the pair of flexible long members without the need for a clutch mechanism or the like.

Furthermore, each flexible long member is able to be formed of a wire or the like, thereby easily enabling a reduction in size or weight of the limb motion support device.

In the above 19th invention, the following embodiment may be employed: the motion transmission mechanism is configured to run each of the pair of flexible long members so that the fifth member connected to one of the flexible long members comes close from the other end side of the spring member to one end thereof with an increase in the bending degree of the left limb and the fifth member connected to the other flexible long member comes close from one end side of the spring member to the other end thereof with an increase in the bending degree of the right limb in a state where the bending degrees of the right and left limbs are lower than the first bending degree, and configured to cause an elastic deformation of the spring members in a pulling direction by running the pair of flexible long members in such a way as to increase a distance between the pair of fifth members with an increase in the bending degrees of the right and left limbs with each of the pair of fifth members bound to both ends of the spring member due to an engagement of each of the fifth members with both ends of the spring member in a state where the bending degrees of the right and left limbs are higher than the first bending degree (20th invention)

According thereto, in the case where both of the right and left limbs are bent from the stretched state, motion transmission switching from the pair of braces to the spring member (switching from a state where the elastic deformation of the spring member does not occur to a state where the elastic deformation occurs) is able to be smoothly performed with a simple configuration. In this case, in a state where the bending degrees of the right and left limbs are larger than the first bending degree, the assisting force is able to be applied to the user by an elastic force generated by a tensile deformation of the spring member.

In the above 19th invention, the following embodiment may be employed: one of the flexible long members is disposed in such a way as to extend from one end side of the spring member toward the other end side thereof and the other flexible long member is disposed in such a way as to extend from the other end side of the spring member toward one end side thereof; and the motion transmission mechanism is configured to run each of the pair of flexible long members so that the fifth member connected to one of the flexible long members comes close from the opposite side (the outside) of one end of the spring member to the other end thereof with an increase in the bending degree of the left limb and the fifth member connected to the other flexible long member comes close from the opposite side of the other end of the spring member to one end thereof with an increase in the bending degree of the right limb in a state where the bending degrees of the right and left limbs are lower than the first bending degree, and configured to cause an elastic deformation of the spring member in a compression direction by running the pair of flexible long members in such a way as to decrease a distance between the pair of fifth members with an increase in the bending degrees of the right and left limbs with each of the pair of fifth members bound to both ends of the spring member due to an engagement of each of the fifth members with both ends of the spring member in a state where the bending degrees of the right and left limbs are higher than the first bending degree (21st invention).

According thereto, similarly to the fourth invention, in the case where both of the right and left limbs are bent from the stretched state, motion transmission switching from the pair of braces to the spring member (switching from a state where the elastic deformation of the spring member does not occur to a state where the elastic deformation occurs) is able to be smoothly performed with a simple configuration. In this case, in the case where the bending degrees of the right and left limbs are larger than the first bending degree, an assisting force is able to be applied to the user by an elastic force generated by the compressive deformation of the spring member.

In the above 20th invention, preferably, preferably the spring member is movably arranged between a position in which one end of the spring member engages with one of the pair of fifth members and a position in which the other end of the spring member engages with the other of the pair of fifth members (22nd invention). This also applies to the 21st invention (23rd invention).

According thereto, in the case where one limb out of the right and left limbs is stretched while the other limb is bent, the bending degree on the upper limit side of the range of the bending degree of the other leg in which the movements of the pair of braces are not transmitted to the spring member is able to be made larger than the first bending degree.

Therefore, particularly in the case where the right and left limbs are the right and left legs of the user, it is possible to prevent the elastic force of the spring member from being generated or to prevent the elastic force from being generated as much as possible.

In the above 19th to 23rd inventions, if the right and left limbs are right and left legs of the user, preferably each of the pair of flexible long members is disposed in such a way that the path length increases according to an increase in a bending degree of each leg at a knee of the user (24th invention).

According thereto, when both legs of the user are bent at the respective knees, the elastic force of the spring member is able be generated.

In the above 24th invention, further, preferably each of the pair of flexible long members is disposed in such a way that the path length increases according to an increase in the bending degree of each leg at the knee of the user and an increase in the bending degree of the leg at the hip joint (25th invention).

According thereto, not only when both legs of the user are bent at the respective knees, but also when the legs are bent at the respective hip joints with respect to the body, the elastic forces of the spring members are able to be generated. Moreover, when the user bends the legs at both of the respective knees and hip joints such as when sitting in a chair or the like or squatting, the first bending degree at which the generation of the elastic forces of the spring members is started can be made smaller than the case where the pair of flexible long members are disposed so that the path length is not affected by the bending of the legs at the respective hip joints of the user.

For example, regarding the bending of each leg at the hip joint in walking of the user, one leg is bent at the hip joint thereof while the other leg moves so as to be stretched at the hip joint thereof. Therefore, a change in the path length of each of the pair of flexible long members, which is caused by the bending of the legs at the hip joints, is counteracted. This enables the prevention of a change in the path length of each of the pair of flexible long members in walking of the user. Consequently, the elastic force of the spring member is not generated in walking of the user or the generation can be easily prevented.

In the above 19th to 25th inventions, preferably each of the pair of braces is provided with a circular or eccentric cam-shaped pulley, which rotates in response to the bending of the limb to which each of the braces is attached, and one of the flexible long members is disposed via the outer periphery of the pulley installed in the brace attached to the left limb out of the right and left limbs and the other flexible long member is disposed via the outer periphery of the pulley installed in the brace attached to the right limb out of the right and left limbs (26th invention).

According thereto, it is possible to easily change the path length of each of the pair of flexible long members in a part of the section according to the bending degree of each of the right and left limbs. Moreover, if the pulley is eccentric cam-shaped, the form of the change in the elastic forces of the spring member relative to the bending degree of each of the right and left limbs can be set to various forms.

In the above 19th to 26th inventions, the following embodiment may be employed: each of the pair of braces has at least two link members connected so as to relatively rotate in response to the bending of the limb equipped with the brace and a circular pulley rotatably supported by one of the two link members around the rotation axis in a position offset from the rotation axis of the relative rotation of the two link members; and each of the pair of flexible long members is disposed via an outer periphery of the pulley of each of the pair of braces (27th invention).

According thereto, a frictional force generated between each of the pair of flexible long members and the pulley of each brace is able to be reduced at the time of bending the right and left limbs. Thereby, an energy loss caused by the friction is able to be reduced.

In the above 19th to 27th inventions, preferably the spring member is arranged so as to expand and contract in a right-and-left direction on a back side or a front side of a body of the user (28th invention).

According thereto, the spring member and the pair of flexible long members can be arranged in a compact and well-balanced manner. Furthermore, in the case where the spring member is arranged on the front side of the body of the user, the limb motion support device according to the present invention is able to be easily attached to the body of the user even if the user is in a sitting position.

In the above third, fourth, seventh, ninth, 11th, 13th, 15th, or 17th inventions, preferably the limb motion support device further includes a first bending degree control mechanism which changes the first bending degree (29th invention). This also applies to the fifth, sixth, 8th, 10th, 12th, 14th, 16th, or 18th invention (30th invention). Furthermore, it also applies to 19 to 28th inventions (31st invention).

According thereto, the first bending degree is able to be appropriately adjusted in a variable manner.

In the above 29th invention, the following embodiment may be employed: the first bending degree control mechanism includes a mechanism which changes the path length in a part of a section of the flexible long member (32nd invention). This also applies to the 30th invention (33rd invention).

Moreover, in the above 31st invention, the following embodiment may be employed: the first bending degree control mechanism includes a mechanism which changes the path length in a part of a section of at least one of the pair of flexible long members (34th invention).

According to the 32nd, 33rd, and 34th inventions, the first bending degree control mechanism is able to be achieved with a simple configuration.

Furthermore, in the above 32nd invention, the first bending degree control mechanism may include an actuator that generates a driving force for changing the path length (35th invention). This also applies to the above 33rd invention (36th invention). Furthermore, it also applies to the above 34th invention (37th invention).

The driving force necessary for changing the path length may be generally a small driving force. Therefore, an actuator such as a compact and lightweight electric motor is able to be employed as the actuator. Accordingly, even if the limb motion support device according to the present invention includes the actuator, the limb motion support device having a lightweight and simple configuration is achieved.

DESCRIPTION OF THE PREFERRED EMBODIMENTS

First Embodiment

Figure 1:
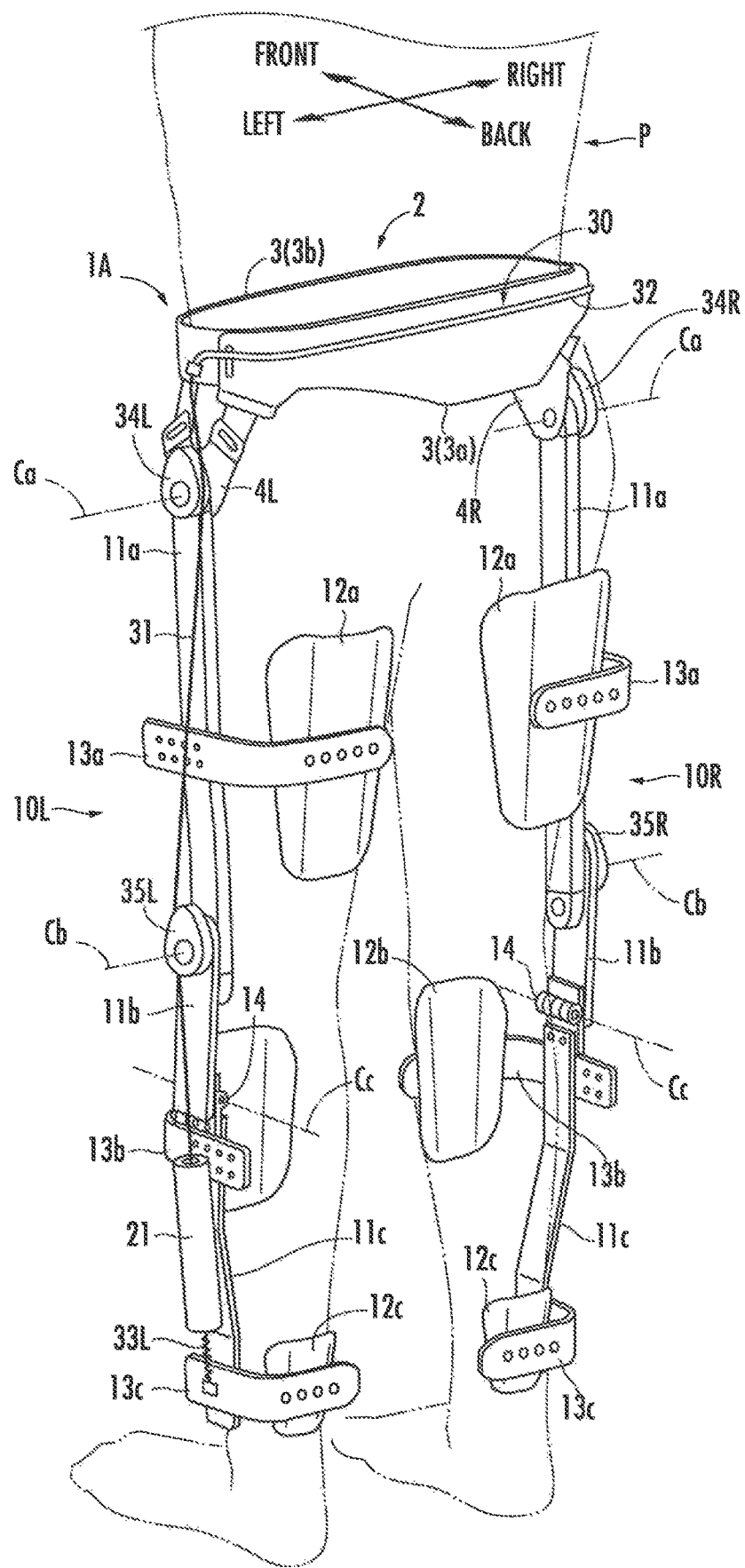
FIG. 1 is a perspective view illustrating an overall structure of a limb motion support device according to a first embodiment (or a second embodiment) of the present invention.

A first embodiment of the present invention will be described hereinbelow with reference to FIGS. 1 to 4. Referring to FIG. 1, a limb motion support device 1A of this embodiment is a device which supports bending and stretching motions of the right and left legs as the right and left limbs of a user P.

This limb motion support device 1A (hereinafter, simply referred to as "motion support device 1A") has a function of generating assisting forces in a direction of stretching the legs if the bending degrees of the legs increase to a certain degree or more in the case where the user P bends the legs to relatively large bending degrees, such as in the case where the user P sits in a chair or the like or squats in a Hindu squat exercise or the like. Furthermore, the motion support device 1A has a function of substantially preventing the generation of the aforementioned assisting force (the assisting force is zero or sufficiently small) in the case where the bending degrees of the legs of the user P are small. In addition, the motion support device 1A is configured to be able to implement these functions without the need for an actuator such as an electric motor or the like.

Furthermore, the motion support device 1A is configured so that, in the case where the user P stretches one leg while bending the other leg such as in walking or the like of the user P, a range of the bending degree of one leg, in which the above assisting force is not substantially generated, is wider than in the case where both legs of the user P are bent Hereinafter, to be more specific, the motion support device 1A includes a body attachment member 2, which is attached to the body of the user P, a pair of right and left leg link mechanisms 10R and 10L, which are extended from the right and left side parts of the body attachment member 2, respectively, as braces attached to the right and left legs of the user P, a pair of right and left spring members 20R and 20L (illustrated in FIG. 2) capable of generating elastic forces for supporting the motions of the legs of the user P, and a motion transmission mechanism 30, which transmits the bending and stretching motion (the bending and stretching motion at the knees and hip joints) of the legs of the user P to the spring members 20L and 20R so as to allow the generation of the elastic forces of the spring members 20L and 20R in response to the bending of the legs (one or both legs) of the user P.

Regarding the reference numerals of the constituent elements of the motion support device 1A in the description of this embodiment, a reference numeral with "L" appended to the end thereof means a reference numeral of an element related to a motion or a configuration of the leg link mechanism 10L on the left leg side of the user P, while a reference numeral with "R" appended to the end thereof means a reference numeral of an element related to a motion or a configuration of the leg link mechanism 10R on the right leg side of the user P. If, however, there is no need to distinguish between right and left or if it is clear to which of the leg link mechanisms 10L and 10R the element is related, appending "L" or "R" is often omitted. This is the same as in other embodiments described later.

The body attachment member 2 is configured so as to be attachable to, for example, a waist of the body of the user P in this embodiment. The body attachment member 2 has a loop-shaped member 3 including a hip pad member 3a to be placed in contact with the back of the waist of the user P and a belt member 3b connected to the right and left side parts of the hip pad member 3a. The body attachment member 2 is then attached to the waist of the user P by wrapping the loop-shaped member 3 around the waist of the user P.

The body attachment member 2 has a pair of right and left mounting plates 4R and 4L, to which the right and left leg link mechanisms 10R and 10L are connected respectively. These mounting plates 4R and 4L are connected to the loop-shaped member 3 so as to be opposed to the right and left side parts of the waist, respectively, in the positions of the same height as the hip joint portions of the right and left legs of the user P with the loop-shaped member 3 attached to the waist of the user P.

In addition, the body attachment member 2 may be configured to be attached to the body on the upper side than the waist of the user P. The attaching structure of the body attachment member 2 to the body of the user P may be different from the above structure as long as the structure is able to keep the position of the body attachment member 2 to the body almost constant.

The leg link mechanisms 10L and 10R are bilaterally symmetric, each having the same structure. Each leg link mechanism 10 includes a first link 11a, a second link 11b, and a third link 11c, which are sequentially connected from the mounting plate 4 (the mounting plate 4 on the same side as the leg link mechanism 10) of the body attachment member 2, and a first leg support member 12a, a second leg support member 12b, and a third leg support member 12c, which are brought into contact with the back part of a thigh of the leg of the user P (the leg on the same side as the leg link mechanism 10), the front part of the upper part of the crus, and the back part of the lower part of the crus, respectively.

In the following description related to the structure of each leg link mechanism 10, a term "leg of the user P" means a leg on the same side (left or right) as the leg link mechanism 10, unless otherwise specified.

The first link 11a of each leg link mechanism 10 is a link arranged so as to extend in the longitudinal direction of the thigh on the lateral side of the thigh of the leg of the user P. The first link 11a has an upper end that is rotatably supported by the mounting plate 4 so as to be swingable around a swing axis Ca in the horizontal direction with respect to the mounting plate 4.

The second link 11b is a link arranged so as to extend in the longitudinal direction of the crus on the lateral side of the upper part of the crus of the leg of the user P. The second link 11b has an upper end that is rotatably supported by the lower end of the first link 11a so as to be swingable around a swing axis Cb in the horizontal direction with respect to the first link 11a.

The third link 11c is a link arranged so as to extend in the longitudinal direction of the crus on the lateral side of the lower part of the crus of the leg of the user P. The third link 11c has an upper end that is connected to the second link 11b via a hinge 14 so as to be swingable around a swing axis Cc in the anteroposterior direction with respect to the second link 11b. The hinge 14 is used to reduce the restrained feeling between the leg of the user P and the leg link mechanism 10. In addition, the second link 11b and the third link 11c may be unified without using the hinge 14.

The first leg support member 12a is mounted on the distal end of the arm member 13a extended so as to go around the back side of the thigh of the leg of the user P from the middle part of the first link 11a.

The second leg support member 12b is mounted on the distal end of the arm member 13b extended so as to go around the front side of the crus of the leg of the user P from the upper part of the third link 11c.

The third leg support member 12c is mounted on the distal end of the arm member 13c extended so as to go around the back side of the crus of the leg of the user P from the lower part of the third link 11c.

In addition, the mounting structure of the first leg support member 12a to the first link 11a may be configured so as to enable the adjustment of the relative position of the first leg support member 12a with respect to the first link 11a. This is the same as for the mounting structure of each of the second leg support member 12b and the third leg support member 12c with respect to the third link 11c.

Each leg link mechanism 10 is configured as described above. Accordingly, each leg link mechanism 10 is attached to the leg of the user P so as to move with the leg by attaching the loop-shaped member 3 of the body attachment member 2 to the body (waist) of the user P and bringing the first to third leg support members 12a, 12b, and 12c of each leg link mechanism 10 into contact with the back part of the thigh, the front part of the upper part of the crus, and the back part of the lower part of the crus of the leg (the leg on the same side as the leg link mechanism 10) of the user P, respectively.

In this case, according to a swing (a swing in the pitch direction at the hip joint) of each leg with respect to the body of the user P, the first link 11a of the leg link mechanism 10 on the same side as the leg swings around the swing axis Ca with respect to the body attachment member 2. Thereby, the first link 11a moves with the thigh in such a way as to keep the positional relationship with the thigh of the leg of the user P almost constant.

Moreover, according to a swing (a swing in the pitch direction at the knee joint) of the crus with respect to the thigh of each leg of the user P, the second link 11b and the third link 11c of the leg link mechanism 10 on the same side as the leg swing around the swing axis Cb with respect to the first link 11a. Thereby, the second link 11b and the third link 11c move with the crus so as to keep the positional relationship with the crus of the leg of the user P almost constant.

In addition, in this embodiment, the second leg support member 12b is arranged so as to come into contact with the front part of the upper part of the crus (the front part close to the knee of the crus) of the leg of the user P. The second leg support member 12b, however, may be arranged so as to come into contact with, for example, the front part of the knee of the leg of the user P or the front part of the lower part of the thigh (the front part close to the knee of the thigh).

Figure 2:
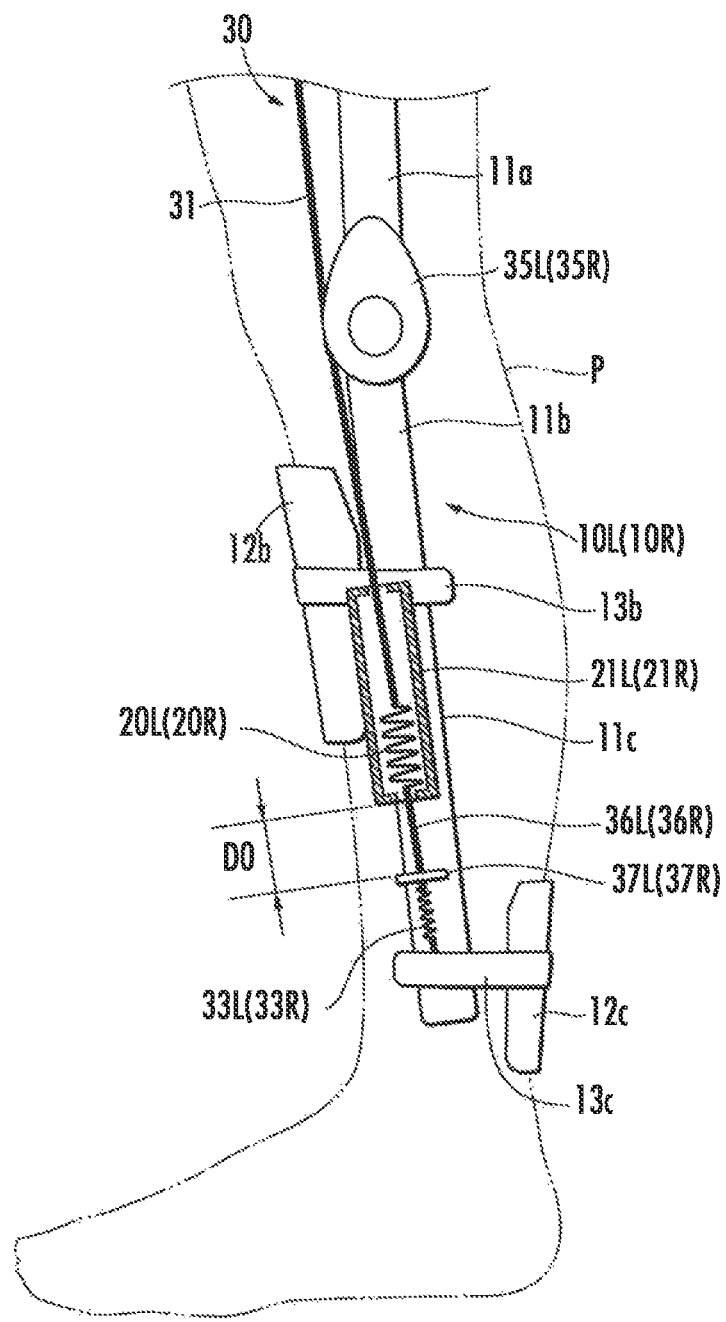
FIG. 2 is a diagram illustrating a main structure (a main structure in a state where a limb (leg) is stretched) of the limb motion support device according to the first embodiment.
Figure 3:
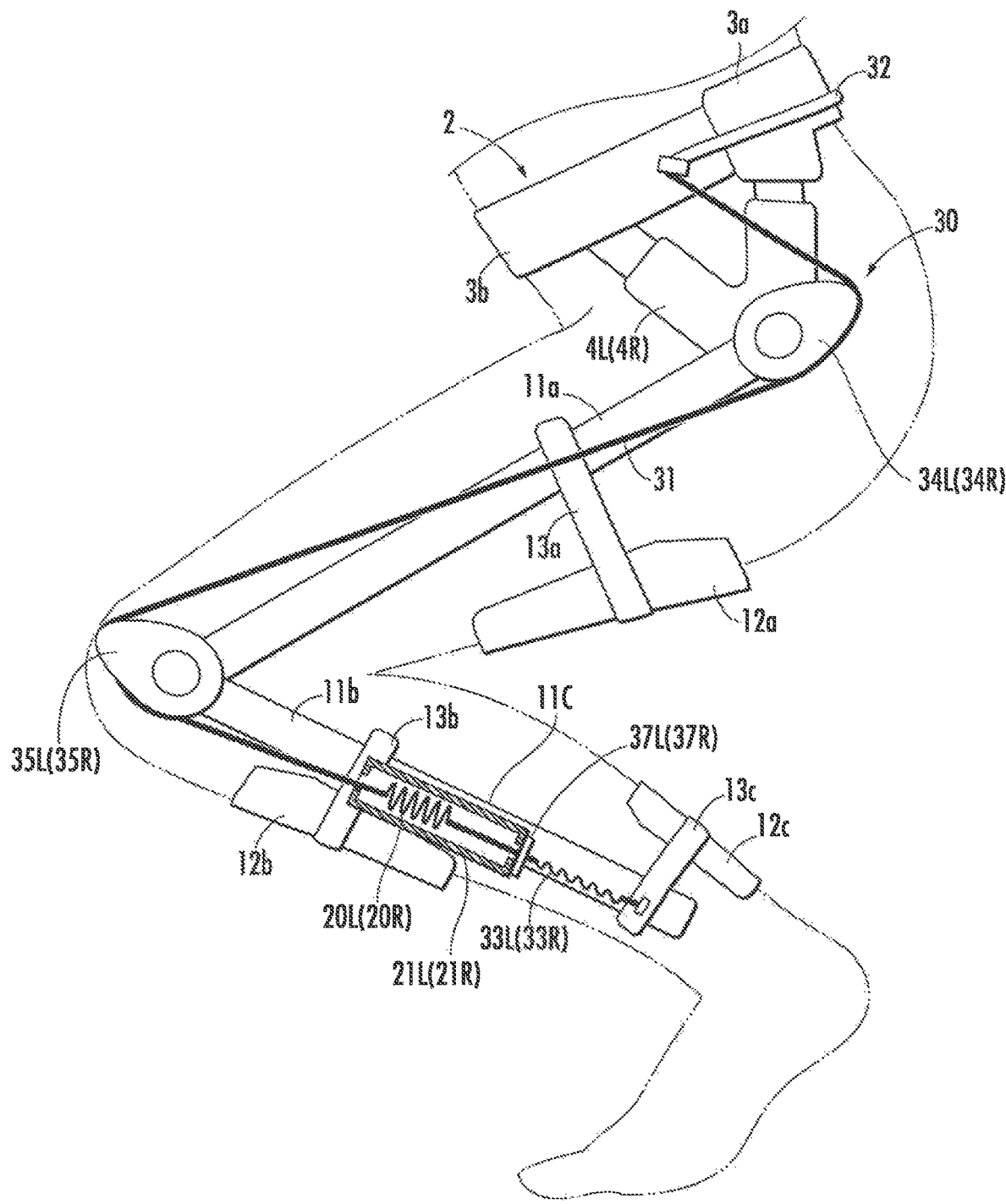
FIG. 3 is a diagram illustrating a main structure (a main structure in a state where a limb (leg) is bent) of the limb motion support device according to the first embodiment.

The spring members 20L and 20R are spring members having the same specifications as each other. In this embodiment, each spring member 20 is formed of, for example, a coil spring as illustrated in FIG. 2 or 3. Furthermore, the spring members 20L and 20R are installed in the leg link mechanisms 10L and 10R, respectively.

In more detail, in this embodiment, a hollow guide tube 21 is mounted on the third link 11c of each leg link mechanism 10 and each spring member 20 is housed in the guide tube 21 as illustrated in FIG. 2 or 3.

While FIGS. 2 and 3 each illustrate the constituent elements installed in the left leg link mechanism 10L, the constituent elements installed in the right leg link mechanism 10R are the same as those of the left leg link mechanism 10L. Therefore, in FIGS. 2 and 3, the reference numerals in the main structure installed in the right leg link mechanism 10R are indicated by parenthesized reference numerals.

The above guide tube 21 is arranged so as to extend in the longitudinal direction of the third link 11c along the third link 11c of each leg link mechanism 10, with the outer periphery of the guide tube 21 fixed to the third link 11c.

Furthermore, each spring member 20 is able to expand and contract in the axial direction of the aforementioned guide tube 21 and is slidably housed in the guide tube 21 so as to be movable in the axial direction of the guide tube 21 between both ends of the guide tube 21.

In this embodiment, the elastic force generated by each spring member 20 to cause an assisting force to be applied to the user P is also an elastic force generated by the extension (tensile deformation) of the spring member 20.

In this embodiment, the motion transmission mechanism 30 includes a wire 31 as a flexible long member connected to the right and left spring members 20R and 20L, an outer tube 32 slidably covering a part of the wire 31, and a mechanism installed in each of the leg link mechanisms 10L and 10R, as illustrated in FIGS. 1 to 3. In the following description, the mechanism of the motion transmission mechanism 30 installed in the leg link mechanism 10L is referred to as "left-leg side mechanism" and the mechanism installed in the leg link mechanism 10R is referred to as "right-leg side mechanism."

The outer tube 32 is a tubular body having a predetermined length and is arranged so as to extend generally in the horizontal direction on the back side of the hip pad member 3a of the body attachment member 2. Furthermore, the right and left ends of the outer tube 32 are fixed to the right and left side parts of the hip pad member 3a, respectively.

The wire 31 is slidably inserted into the outer tube 32 and is led out from both ends of the outer tube 32. In the following description, the portion led out from the left-side end of the outer tube 32 of the wire 31 is referred to as the left lead-out portion of the wire 31 and the portion led out from the right-side end of the outer tube 32 is referred to as the right lead-out portion of the wire 31, in some cases.

The left-leg side mechanism and the right-leg side mechanism of the motion transmission mechanism 30 have the same structure as each other and include slack eliminating spring members 33L and 33R (see FIG. 2) for applying a weakened tension (pre-tension) to the wire 31, where the weakened tension is intended to eliminate a slack of the wire 31. Each slack eliminating spring member 33 is a spring member having sufficiently smaller rigidity (so-called spring constant) than that of each spring member 20 and is formed of, for example, a coil spring in this embodiment. Each slack eliminating spring member 33, however, may be formed of a spring member other than the coil spring such as, for example, a rubber strap or other rubber member.

Furthermore, the left-leg side mechanism of the motion transmission mechanism 30 is configured so that the left lead-out portion of the wire 31 is connected to the slack eliminating spring member 33L via the left-side spring member 20L. Moreover, the left-leg side mechanism is configured so as to be able to change the path length of the wire 31 in response to the bending and stretching of the left leg of the user P in the disposition section of the wire 31 from the outer tube 32 to the spring member 20L.

Similarly, the right-leg side mechanism of the motion transmission mechanism 30 is configured so that the right lead-out portion of the wire 31 is connected to the slack eliminating spring member 33R via the right-side spring member 20R. Moreover, the right-leg side mechanism is configured so as to be able to change the path length of the wire 31 in response to the bending and stretching of the right leg of the user P in the disposition section of the wire 31 from the outer tube 32 to the spring member 20R.

The following describes in detail the more specific configuration of one of the left-leg side mechanism and the right-leg side mechanism of the motion transmission mechanism 30 such as, for example, the left-leg side mechanism.

In this embodiment, the left-leg side mechanism of the motion transmission mechanism 30 includes a first pulley 34L and a second pulley 35L mounted on the left leg link mechanism 10L as illustrated in FIGS. 1 to 3.

The first pulley 34L is mounted on the first link 11a so as to be rotatable around the swing axis Ca of the first link 11a of the leg link mechanism 10L integrally with the first link 11a. In addition, the second pulley 35L is mounted on the second link 11b so as to be rotatable around the swing axis Cb of the second link 11b of the leg link mechanism 10L integrally with the second link 11b.

The left lead-out portion of the wire 31 reaches the upper end of the guide tube 21L via the outer periphery of the first pulley 34L and that of the second pulley 35L sequentially. Furthermore, the left lead-out portion is introduced into the guide tube 21L passing through a hole formed at the upper end of the guide tube 21L. The distal end of the left lead-out portion of the wire 31 introduced into the inside of the guide tube 21L is then connected to the upper end of the spring member 22L in the guide tube 21L.

Note here that the first pulley 34L and the second pulley 35L are pulleys with the outer periphery formed in an eccentric cam shape. In this case, the outer peripheral shapes of the first pulley 34L and the second pulley 35L are formed so that the path length of the wire 31 (left lead-out portion) from the left-side end of the outer tube 32 to the upper end of the guide tube 21L monotonically increases with an increase in the bending degree of the leg (the bending degree at the knee or the bending degree at the hip joint) when the left leg of the user P equipped with the motion support device 1A is bent from a stretched state.

The slack eliminating spring member 33L included in the left-leg side mechanism of the motion transmission mechanism 30 is connected to the spring member 20L so as to be able to expand and contract with the movement or expansion and contraction of the spring member 20L in the guide tube 21L.

For more detail, in this embodiment, a linear member 36L (a linear member formed of, for example, a wire, a rod, or the like) extended from the lower end of the spring member 20L is led out to below the guide tube 21L, after passing through a hole formed at the lower end of the guide tube 21L. The linear member 36L may be integrated with the spring member 20L.

The distal end (lower end) of the linear member 36L is connected to one end of the slack eliminating spring member 33L via a locking member 37L. The locking member 37L has a larger diameter than the diameter of the hole, into which the linear member 36L is inserted, at the lower end of the guide tube 21L. While the locking member 37L is, for example, a disc-shaped member in the illustrated examples, the locking member 37L may have any other shape as long as it has a size preventing the locking member 37L from passing through the hole at the lower end of the guide tube 21L.

In addition, the other end of the slack eliminating spring member 33L is connected to the arm member 13c (or the lower part of the third link 11c) of the leg link mechanism 10L.

Therefore, in this embodiment, the left-leg side mechanism of the motion transmission mechanism 30 is configured so that the left lead-out portion of the wire 31 is connected to the arm member 13c (or a lower part of the third link 11c) of the leg link mechanism 10L via the outer periphery of the first pulley 34L and that of the second pulley 35L and thereafter via the spring member 20L, the linear member 36L, the locking member 37L, and the slack eliminating spring member 33L sequentially.

In the above case, in this embodiment, the positional relationship between the guide tube 21L and the locking member 37L is set so that a distance D0 having a predetermined value is formed between the lower end of the guide tube 21L and the locking member 37L as illustrated in FIG. 2 in a state where the user P equipped with the motion support device 1A stretches the leg.

The left-leg side mechanism of the motion transmission mechanism 30 is configured as described above. The right-leg side mechanism of the motion transmission mechanism 30 has the same configuration as the left-leg side mechanism. In this case, the right-leg side mechanism of the motion transmission mechanism 30 can be described by replacing the words "left" and "L" in the above description related to the left-leg side mechanism of the motion transmission mechanism 30 with words "right" and "R."

In this embodiment, the lower end of each guide tube 21 corresponds to the first member of the present invention and each locking member 37 corresponds to the second member of the present invention.

Subsequently, the working of the motion support device 1A configured as described above will be described. First, such a case is assumed that the user P equipped with the motion support device 1A bends the legs at the same bending degree as each other from a state in which the legs are stretched.

The motion of bending the legs of the user P in this manner is a motion in a case where, for example, the user P sits in a chair or the like or squats in the Hindu squat exercise or the like. More specifically, this motion is bending the legs at the respective knees and also at the respective hip joints.

In this case, both of the path length of the wire 31 from the left-side end of the outer tube 32 to the upper end of the left guide tube 21L and the path length of the wire 31 from the right-side end of the outer tube 32 to the upper end of the right guide tube 21R increase with an increase in the bending degrees of the legs (the bending degrees at both knees and the bending degrees at both hip joints) of the user P.

Thereby, the spring members 20L and 20R move toward the upper ends of the guide tubes 21L and 21R, respectively. Simultaneously therewith, the locking members 37L and 37R of the motion transmission mechanism 30 come close to the lower ends of the guide tubes 21L and 21R, respectively.

In this situation, the slack eliminating spring members 33L and 33R each having rigidity sufficiently smaller than that of each spring member 20 extend, by which both of the spring members 20L and 20R move to the upper end side thereof in the inside of the guide tubes 21L and 21R substantially without extending (substantially without generating elastic forces). Therefore, the tension of the wire 31 is sufficiently small.

In the motion support device 1A of this embodiment, an assisting force acting in a direction of decreasing the bending degree of the leg (in a direction of stretching the leg) of the user P equipped with the leg link mechanism 10 increases with an increase in the tension of the wire 31 in a state where the leg of the user P equipped with the leg link mechanism 10 (10L or 10R) is bent to some extent. In a state where the tension of the wire 31 is sufficiently small, the assisting force is sufficiently small.

Therefore, in a situation where the locking members 37L and 37R come close to the lower ends of the guide tubes 21L and 21R, respectively, as described above, the tension of the wire 31 is sufficiently small. Accordingly, the assisting forces in a direction of stretching the legs of the user P are substantially not generated (the assisting forces are only sufficiently small).

In the stretched state of the legs of the user P equipped with the leg link mechanism 10 (10L or 10R) (the stretched state of the leg link mechanism 10), the wire 31 to be in contact with the second pulley 35L extends approximately linearly. Therefore, not only when the tension of the wire 31 is small, but also when the tension is relatively large, the force which changes the bending degree of the leg of the user P equipped with the leg link mechanism 10 is sufficiently small.

If the bending degrees of the legs of the user P further increase, the locking members 37L and 37R of the motion transmission mechanism 30 are eventually locked in contact with the respective lower ends of the guide tubes 21L and 21R as illustrated in FIG. 3.

When both of the locking members 37L and 37R are locked in contact with the lower ends of the guide tubes 21L and 21R, respectively, the lower ends of the spring members 20L and 20R are locked to (bound to) the lower ends of the guide tubes 21L and 21R through the locking members 37L and 37R, respectively.

Therefore, with a further increase in the path length of the wire 31 from the left-side end of the outer tube 32 to the upper end of the left guide tube 21L and the path length of the wire 31 from the right-side end of the outer tube 32 to the upper end of the right guide tube 21R as the bending degrees of the legs of the user P further increase, the spring members 20L and 20R are pulled by the wire 31 and thereby the spring members 20L and 20R are extended. Consequently, each of the spring members 20L and 20R generates an elastic force in a shortening direction. The elastic force and the tension of the wire 31 then increase with a further increase in the bending degrees of the legs of the user P.

Furthermore, the increase in the tension of the wire 31 causes a force in the stretching direction to act on each of the leg link mechanisms 10L and 10R via the corresponding second pulley 35L or 35R. Consequently, assisting forces in the stretching direction act on the legs of the user P.

In the case where the legs of the user P are bent as described above, the elastic forces of the spring members 20L and 20R are substantially not generated until the bending degrees of the legs reach a predetermined bending degree (the bending degree at which both of the locking members 37L and 37R are locked in contact with the lower ends of the guide tubes 21L and 21R, respectively). Therefore, the assisting forces do not act on the legs of the user P substantially.

Thereafter, if the bending degrees of the legs of the user P exceed the predetermined bending degree, the elastic forces of the spring members 20L and 20R are generated. Accordingly, the tension of the wire 31 increases. Consequently, the assisting forces in the stretching direction act on the legs of the user P.

Subsequently, such a case is assumed that the user P equipped with the motion support device 1A maintains one leg such as, for example, the right leg in the stretched state (or a state close thereto), while bending the other leg (the left leg in this specification).

In this case, the right leg of the user P is maintained in the stretched state (or a state close thereto), thereby maintaining the path length of the wire 31 from the right-side end of the outer tube 32 to the upper end of the right guide tube 21 constant or substantially constant.

On the other hand, the path length of the wire 31 from the left-side end of the outer tube 32 to the upper end of the left guide tube 21 increases with an increase in the bending degree of the left leg (the bending degree at the knee) of the user P.

Thereby, the right and left spring members 20R and 20L move toward the upper ends of the guide tubes 21R and 21L, respectively. Simultaneously therewith, the locking members 37L and 37R come close to the lower ends of the guide tubes 21L and 21R, respectively.

In this situation, similarly to the bending of the legs of the user P, the elastic forces of the spring members 20L and 20R are substantially not generated (consequently, the tension of the wire 31 is sufficiently small). Therefore, the assisting force does not act on not only the right leg in the stretched state of the user P, but also on the bent left leg of the user P.

If the bending degree of the left leg of the user P further increases, then, both of the locking members 37L and 37R are locked in contact with the lower ends of the guide tubes 21L and 21R, respectively. Hereinafter, the elastic forces of the spring members 20L and 20R are substantially generated similarly to the case of bending both legs of the user P. Therefore, the tension of the wire 31 increases. Consequently, the assisting force in the stretching direction acts on the left leg of the user P. Additionally, the right leg of the user P is placed in the stretched state (or a state close thereto). Accordingly, even if the tension of the wire 31 increases, a force in the direction of changing the bending degree of the right leg is not substantially generated (the force is sufficiently small).

The above working also applies to the case of bending the right leg while keeping the left leg of the user P in the stretched state (or a state close thereto).

In this manner, even in the case of bending only one leg of the user P, no assisting force substantially acts on the legs of the user P until the bending degree of the bent leg reaches a predetermined bending degree (the bending degree at which both of the locking members 37L and 37R are locked in contact with the lower ends of the guide tubes 21L and 21R, respectively). Thereafter, if the bending degree of the bent leg exceeds the predetermined bending degree, the assisting force in the stretching direction acts on the leg.

Note that, however, in the case of bending only one leg of the user P, only one of the path length of the wire 31 from the left-side end of the outer tube 32 to the upper end of the left guide tube 21L and the path length of the wire 31 from the right-side end of the outer tube 32 to the upper end of the right guide tube 21R increases with an increase in the bending degrees of the legs of the user P, as described above.

Therefore, in the case of bending only one leg of the user P, the bending degree of one leg at which the elastic forces of the spring members 20L and 20R start to be substantially generated (the bending degree at which both of the locking members 37L and 37R are locked in contact with the lower ends of the guide tubes 21L and 21R, respectively) is larger than the bending degree in the case of bending both legs of the user P.

Figure 4:
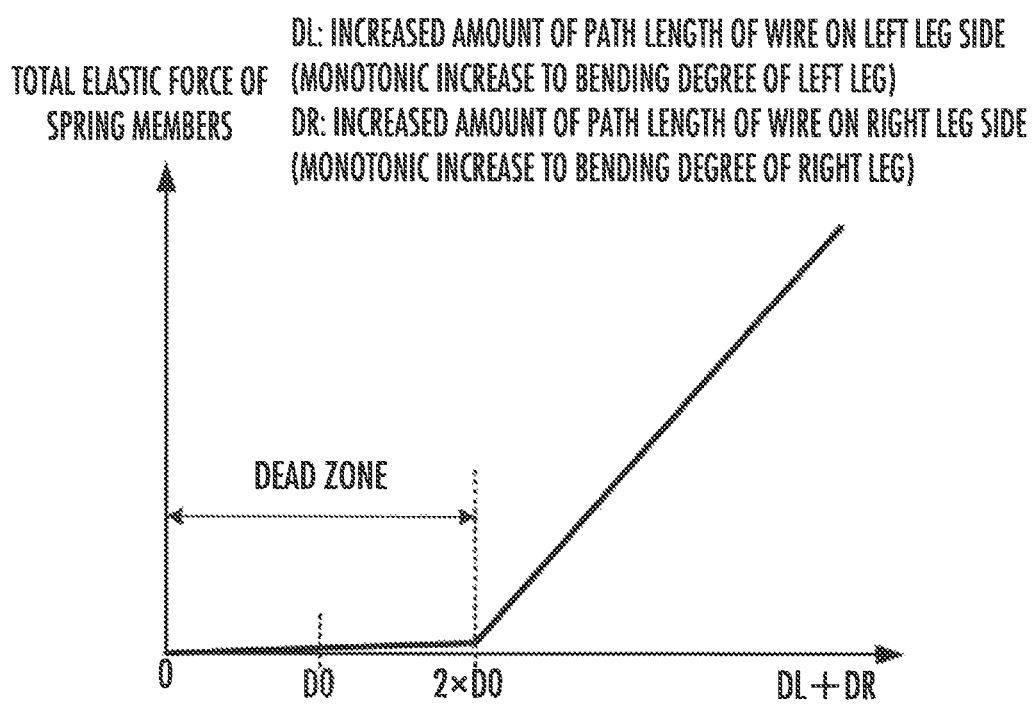
FIG. 4 is a diagram illustrating variation characteristics of an elastic force of a spring member of the limb motion support device according to the first embodiment (or the second embodiment)

Due to the working as described above, the total elastic force of the spring members 20L and 20R (the total sum of the elastic force of the spring member 20L and the elastic force of the spring member 20R) basically changes in the pattern as illustrated in the graph of FIG. 4.

In the graph, DL indicates the increased amount of the path length of the wire 31 from the left-side end of the outer tube 32 to the upper end of the left guide tube 21L (the amount of increase associated with an increase in the bending degree from the stretched state of the left leg of the user P) and DR indicates the increase amount of the path length of the wire 31 from the right-side end of the outer tube 32 to the upper end of the right guide tube 21R (the amount of increase associated with an increase in the bending degree from the stretched state of the right leg of the user P).

Moreover, as illustrated in FIG. 2, D0 indicates a distance (a predetermined value) between each of the locking members 37L and 37R in a state where the legs of the user P are stretched (a state where both of the leg link mechanisms 10L and 10R are stretched) and each of the lower ends of the guide tubes 21L and 21R.

In FIG. 4, the state satisfying an inequality "DL+DR<2× D0" in FIG. 4 is a state in which the locking members 37L and 37R are movable toward the lower ends of the guide tubes 21L and 21R, respectively (in other words, a state in which the spring members 20L and 20R are movable in the guide tubes 21L and 21R without extending. In this state, even if the bending degrees of the legs of the user P change, the spring members 20L and 20R substantially do not generate elastic forces. Therefore, a range where the bending degrees of the legs of the user P satisfy the inequality "DL+DR<2×D0" is a dead zone in which the respective assisting forces substantially do not act on the legs of the user P.

Furthermore, a state satisfying an inequality "DL+DR≥2× D0" is a state in which the lower ends of the spring members 20L and 20R are locked to the lower ends of the guide tubes 21L and 21R via the locking members 37L and 37R, respectively. In this state, the total elastic force of the spring members 20L and 20R increase with an increase in the bending degrees of the legs of the user P (consequently, with an increase in DL+DR). Accordingly, the assisting force in the stretching direction acts on each bent leg of the user P.

Then, in the case of keeping one leg (supporting leg) in the stretched state or in a state close thereto with the other leg (free leg) bent as in walking of the user P, "DL+DR≈DL" or "DL+DR≈DR" is satisfied. Therefore, "DL+DR=2×D0" is satisfied and the bending degree of the other leg, at which the elastic forces of the spring members 20L and 20R start to be generated, is relatively large.

Regarding the bending of each leg at the hip joint (the bending to the body) in walking of the user P, one leg is bent at the hip joint while the other leg moves so as to be stretched at the hip joint. Therefore, a change in the path length of the wire 31, which is caused by the bending of the legs at the hip joints, is counteracted. Accordingly, the value of "DL+DR" can be easily relatively small.

On the other hand, when the user P bends the legs at the same bending degree such as a case of sitting in a chair or the like or squatting, "DL+DR≈2×DL (≈2×DR)" is satisfied. Accordingly, the equation "DL+DR=2×D0" is satisfied and the bending degrees of the legs at which the elastic forces of the spring members 20L and 20R start to be generated are smaller than in the case of bending only one leg.

Therefore, the distance D0 of the predetermined value is able to be set so that the value of "DL+DR" is within a range expressed by "DL+DR<2×D0" as much as possible (accordingly, the elastic forces of the spring members 20L and 20R are substantially not generated), for example, in walking of the user P. This prevents the assisting forces from acting on the legs of the user P during walking. Consequently, the user P is able to walk in much the same way as in the normal walking without feeling uncomfortable.

Moreover, when the user P bends the legs at the same bending degree such as a case of sitting in a chair or the like or squatting, the distance D0 of the predetermined value is able to be set so that the value of "DL+DR" satisfies "DL+DR≥2×D0" from a state of the bending degree in the middle of bending both legs. This enables assisting forces in the stretching direction to act on the legs of the user P when the user P sits in a chair or the like or squats. Therefore, the user P is able to easily stand up from a sitting state or a squatting state.

Furthermore, when the user P sits in a chair or the like or squats, the legs are bent also at the hip joints as well as at the knees. Therefore, according to the motion support device 1A of this embodiment, the path lengths of the left lead-out portion and the right lead-out portion of the wire 31 smoothly increase with an increase in the bending degrees of the legs of the user. Therefore, the elastic forces of the spring members 20L and 20R are able to be substantially generated at relatively small bending degrees.

Furthermore, the motion support device 1A is able to generate assisting forces without the need for an actuator such as an electric motor. Moreover, the motion support device 1A performs the motion transmission with the motion transmission mechanism 30 by using the wire 31. Accordingly, the motion support device 1A has a lightweight and simple configuration. Therefore, the user P equipped with the motion support device 1A is able to perform the walking motion or the like in the same manner as in the normal, without feeling uncomfortable or burdened.

In this embodiment, each end of the wire 31 is connected to the upper end of the spring member 20 in each leg link mechanism 10. Note that, however, each end of the wire 31 may be connected to the lower end of the spring member 20 and the locking member 37 may be removed. In this case, in a state where the legs of the user P are stretched, a distance of a predetermined value is previously formed between the upper end of the spring member 20 and the upper end of the guide tube 21. In such a case, the spring member 20 moves toward the upper end of the guide tube 21 and comes into contact with the upper end of the guide tube 21 with an increase in the bending degree of the leg of the user P. Thereafter, the spring member 20 is compressed with the increase in the bending degree of the leg of the user P, thereby enabling the elastic force of the string member 20 to be generated.

Second Embodiment

Subsequently, a second embodiment of the present invention will be described with reference to FIGS. 5 and 6.

In a limb motion support device 1B of this embodiment, the configurations of the body attachment member 2 and the leg link mechanisms 10L and 10R are the same as those of the first embodiment. Therefore, in this embodiment, the differences from the first embodiment are mainly described and the description of the same matters as the first embodiment is omitted.

The motion support device 1A of the first embodiment is configured to generate elastic forces for applying assisting forces to the user P by using the extension (tensile deformation) of the spring members 20L and 20R. Meanwhile, the limb motion support device 1B (hereinafter, simply referred to as "motion support device 1B") of this embodiment is configured to generate the elastic forces by a compressive deformation of the spring members.

Figure 5:
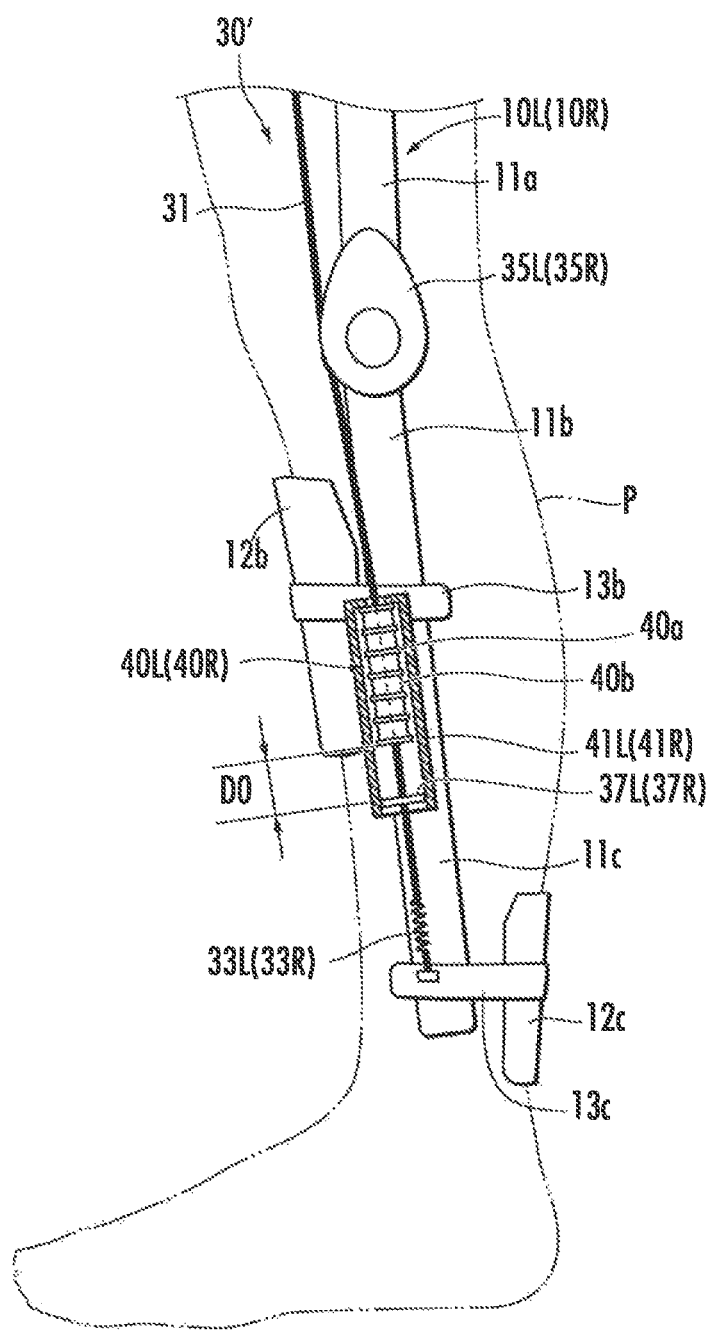
FIG. 5 is a diagram illustrating a main structure (a main structure in a state where a limb (leg) is stretched) of the limb motion support device according to the second embodiment.
Figure 6:
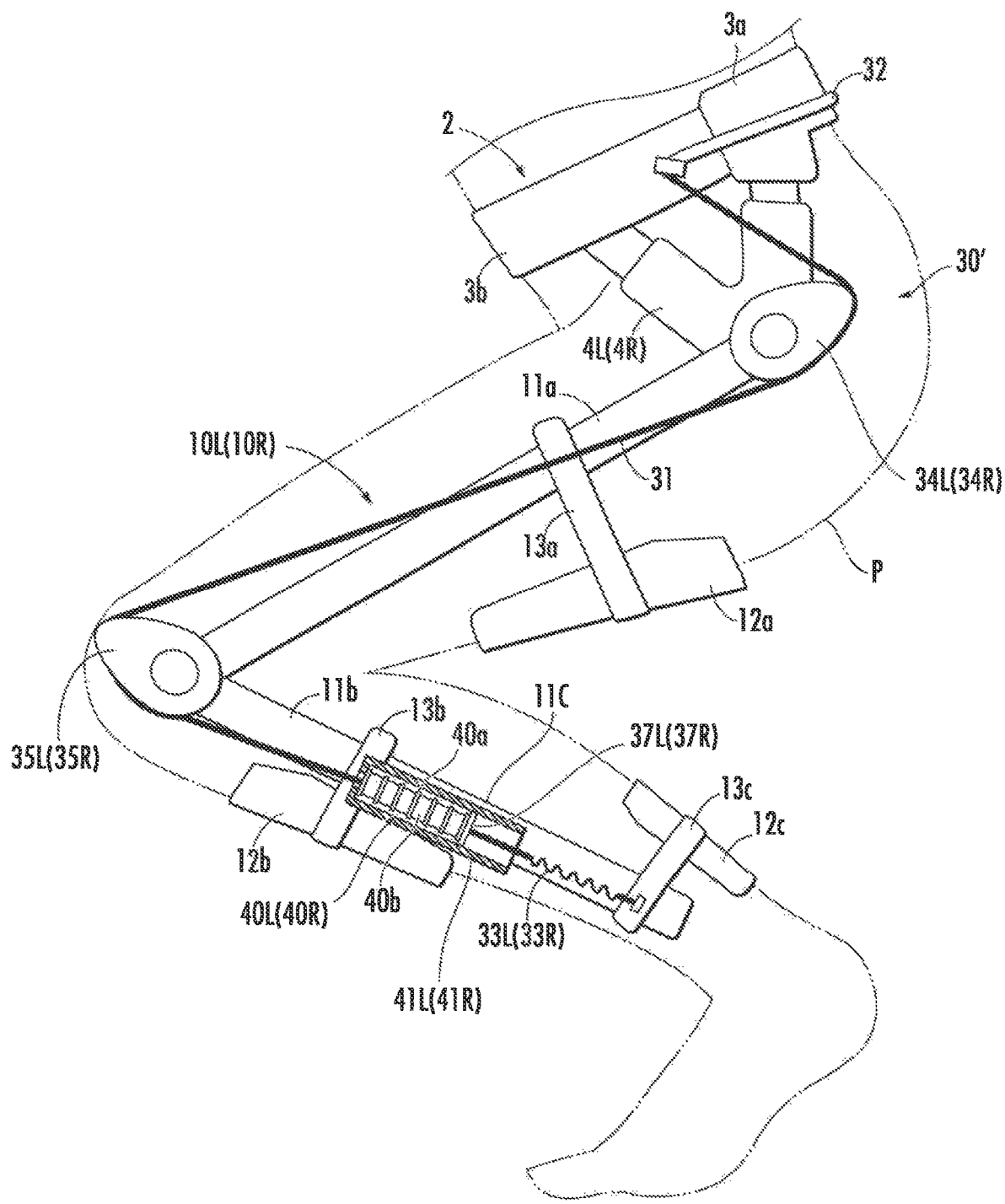
FIG. 6 is a diagram illustrating a main structure (a main structure in a state where a limb (leg) is bent) of the limb motion support device according to the second embodiment.

Specifically, referring to FIGS. 5 and 6, in the motion support device 1B of this embodiment, a spring member 40 and a guide tube 41 having a configuration as illustrated are installed in each leg link mechanism 10, instead of the spring member 20 and the guide tube 21 described in the first embodiment.

Although FIGS. 5 and 6 illustrate the constituent elements installed in the left leg link mechanism 10L, the same applies to the constituent elements installed in the right leg link mechanism 10R. Therefore, in FIGS. 5 and 6, the reference numerals of the main structure installed in the right leg link mechanism 10R are indicated by parenthesized reference numerals, similarly to FIG. 2 and the like described above.

Each spring member 40 is formed by alternately stacking a rigid plate 40a made of metal or the like and a tubular elastic member 40b made of rubber or the like. In this case, the plate 40a and the elastic member 40b in contact with each other are bonded to each other by adhesive or the like. Furthermore, a through-hole (not illustrated) into which the wire 31 is inserted is formed in the axis of the spring member 40. Both ends in the axial direction of the spring member 40 are each formed of the plate 40a.

Each guide tube 41 is arranged along a third link 11c of each leg link mechanism 10 similarly to the guide tube 21 of the first embodiment. Moreover, the outer periphery of the guide tube 41 is fixed to the third link 11c. The guide tube 41 has a hole at the upper end wherein the hole is used to pass the wire 31 through and has an opening (or a hole) having a larger diameter than the locking member 37 described in the first embodiment at the lower end of the guide tube 41.

Furthermore, the spring member 40 is inserted into the guide tube 41 substantially coaxially therewith. Moreover, the plate 40a on one side (the upper end side) of the spring member 40 is fixed to the upper end of the guide tube 41 with the through-hole of the spring member 40 communicated with the hole at the upper end of the guide tube 41.

In this embodiment, the wire 31 and the outer tube 32 are provided to transmit the bending and stretching motion of the legs of the user P to the right and left spring members 40R and 40L in the same manner as in the first embodiment. Furthermore, a motion transmission mechanism 30' includes a slack eliminating spring member 33, a first pulley 34, a second pulley 35, and a locking member 37 as constituent elements of each of a left-leg side mechanism and a right-leg side mechanism of the motion transmission mechanism 30' for each leg link mechanism 10. In the motion transmission mechanism 30' of this embodiment, however, the connection structure for the wire 31, the locking member 37, and the slack eliminating spring member 33 differs from that in the first embodiment.

Specifically, in the motion transmission mechanism 30' of this embodiment, the wire 31 (each of the left lead-out portion and the right lead-out portion) led out from each end of the outer tube 32 goes through the outer peripheries of the first pulley 34 and the second pulley 35, passes through the hole at the upper end of the guide tube 41 so as to be inserted into the through-hole of the spring member 40, thereby passing through the spring member 40. Then, the distal end of the wire 31 led out from the through-hole of the spring member 40 downward is connected to one end of the slack eliminating spring member 33 via the locking member 37.

In the above case, in this embodiment, the positional relationship between the locking member 37 and the spring member 40 is set so that a distance D0 (>0) of a predetermined value is formed between the lower end of the spring member 40 and the locking member 37 in a state where the user P equipped with the motion support device 1B stretches both legs, as illustrated in FIG. 5.

In this embodiment, the locking member 37 has a larger diameter than the diameter of the through-hole of the spring member 40.

The motion support device 1B of this embodiment is the same as the motion support device 1A of the first embodiment except for the matters described above.

In this embodiment, the upper end of each guide tube 21 corresponds to the third member of the present invention and each locking member 37 corresponds to the fourth member of the present invention.

In this embodiment as described above, when the user P equipped with the motion support device 1B bends one leg or both legs, one or both of the path length of the wire 31 from the left-side end of the outer tube 32 to the upper end of the left guide tube 21L and the path length of the wire 31 from the right-side end of the outer tube 32 to the upper end of the right guide tube 21R increase, similarly to the first embodiment.

Then, with an increase in one or both of the path lengths, the locking members 37L and 37R come close to the lower ends of the spring members 40L and 40R, respectively. Eventually, as illustrated in FIG. 6, the locking members 37L and 37R are locked in contact with the lower ends of the spring members 40L and 40R, respectively. Consequently, the wire 31 is bound to the lower ends of the spring members 40L and 40R via the locking members 37L and 37R, respectively.

As described above, after the locking members 37L and 37R are locked in contact with the lower ends of the spring members 40L and 40R, respectively, the locking members 37L and 37R move toward the upper ends of the guide tubes 41L and 41R while pressing the spring members 40L and 40R toward the upper ends of the guide tubes 41L and 41R, respectively, with a further increase in the bending degree of one leg or both legs of the user P. Thereby, the respective elastic members 40b of the spring members 40L and 40R are compressed and then elastic forces are generated. The elastic forces and the tension of the wire 31 then increase. Consequently, assisting forces in the stretching direction act on the bent legs of the user P, similarly to the first embodiment.

In addition, similarly to the first embodiment, in the case of bending only one leg of the user P, the bending degree of one leg at which the elastic forces of the spring members 40L and 40R start to be substantially generated (the bending degree at which both of the locking members 37L and 37R are locked in contact with the lower ends of the spring members 40L and 40R, respectively) is larger than the bending degree in the case of bending both legs of the user P.

Also in this embodiment, the relationship between the total sum (=DL+DR) of the increased amount DL of the path length of the wire 31 from the left-side end of the outer tube 32 to the upper end of the left guide tube 41L and the increased amount DR of the path length of the wire 31 from the right-side end of the outer tube 32 to the upper end of the right guide tube 41R and the total elastic force generated by the spring members 40L and 40R is as illustrated in FIG. 4 similarly to the first embodiment. In this embodiment, D0 indicates a distance D0 (predetermined value) between the lower end of each spring member 40 and the locking member 37.

Additionally, the distance D0 (predetermined value) between the lower end of each spring member 40 and the locking member 37 in a state where both legs of the user P are stretched is preset in the same manner as in the first embodiment, thereby achieving the same advantageous effects as in the first embodiment.

Furthermore, the motion support device 1B has a lightweight and simple configuration similarly to the configuration of the first embodiment. Therefore, the user P equipped with the motion support device 1B is able to perform the walking motion or the like in the same manner as in the normal, without feeling uncomfortable or burdened.

In this embodiment, the distance D0 between the lower end of each spring member 40 and the locking member 37 is formed in a state where both legs of the user P are stretched (the stretched state of both of the leg link mechanisms 10L and 10R). Note that, however, the lower end of each spring member 40 and the locking member 37 are placed in contact with each other (or fixed to each other) in the stretched state of both of the leg link mechanisms 10L and 10R, for example. Furthermore, a distance is formed between the upper end of each spring member 40 and the upper end of the guide tube 41. Thereby, the spring member 40 may be configured to be movable toward the upper end of the guide tube 41.

In addition, although the spring member 40 having the aforementioned structure has been used in this embodiment, the spring member 40 may be a rubber member such as a coil spring or the like.

Furthermore, for example, the configuration as described below may be employed. Specifically, in each leg link mechanism 10, for example, the lower end of the spring member 40 is fixed to the lower end of the guide tube 41. Furthermore, a distance (a distance enabling the spring member 40 to extend) is formed in advance between the upper end of the spring member 40 and the upper end of the guide tube 41.

Additionally, the insertion hole for the wire 31 at the upper end of the spring member 40 having a small diameter is formed in advance. Furthermore, a locking member, having a size inhibiting the locking member from passing through the insertion hole at the upper end of the spring member 40, is fixed to the wire 31, instead of the locking member 37. In this case, the locking member is arranged so as to have a distance of a predetermined value from the upper end of the spring member 40 in the state where both legs of the user P are stretched.

In such a case, the locking member inside the spring member 20 moves toward the upper end of the spring member 40 and comes into contact with the upper end of the spring member 40 with an increase in the bending degree of the leg of the user P. Thereafter, the spring member 40 is pulled and extends with the increase in the bending degree of the leg of the user P, thereby enabling the elastic force of the string member 40 to be generated.

Third Embodiment

Subsequently, a third embodiment of the present invention will be described with reference to FIGS. 7 to 11. In a limb motion support device 1C of this embodiment, the configurations of the body attachment member 2 and the leg link mechanisms 10L and 10R are the same as those of the first embodiment. Therefore, in this embodiment, the differences from the first embodiment are mainly described and the description of the same matters as the first embodiment is omitted.

In the first embodiment, there has been described the motion support device 1A in which the spring members 20L and 20R are installed in the leg link mechanisms 10L and 10R, respectively. Meanwhile, in the limb motion support device 1C (hereinafter, simply referred to as "motion support device 1C") of this embodiment, a single spring member 50 is installed in a body attachment member 2. Accordingly, in the motion support device 1C of this embodiment, the configuration of a motion transmission mechanism 60, which transmits the bending and stretching motion of the legs of the user P to the spring member 50, differs from the configuration of the first embodiment.

Figure 7:
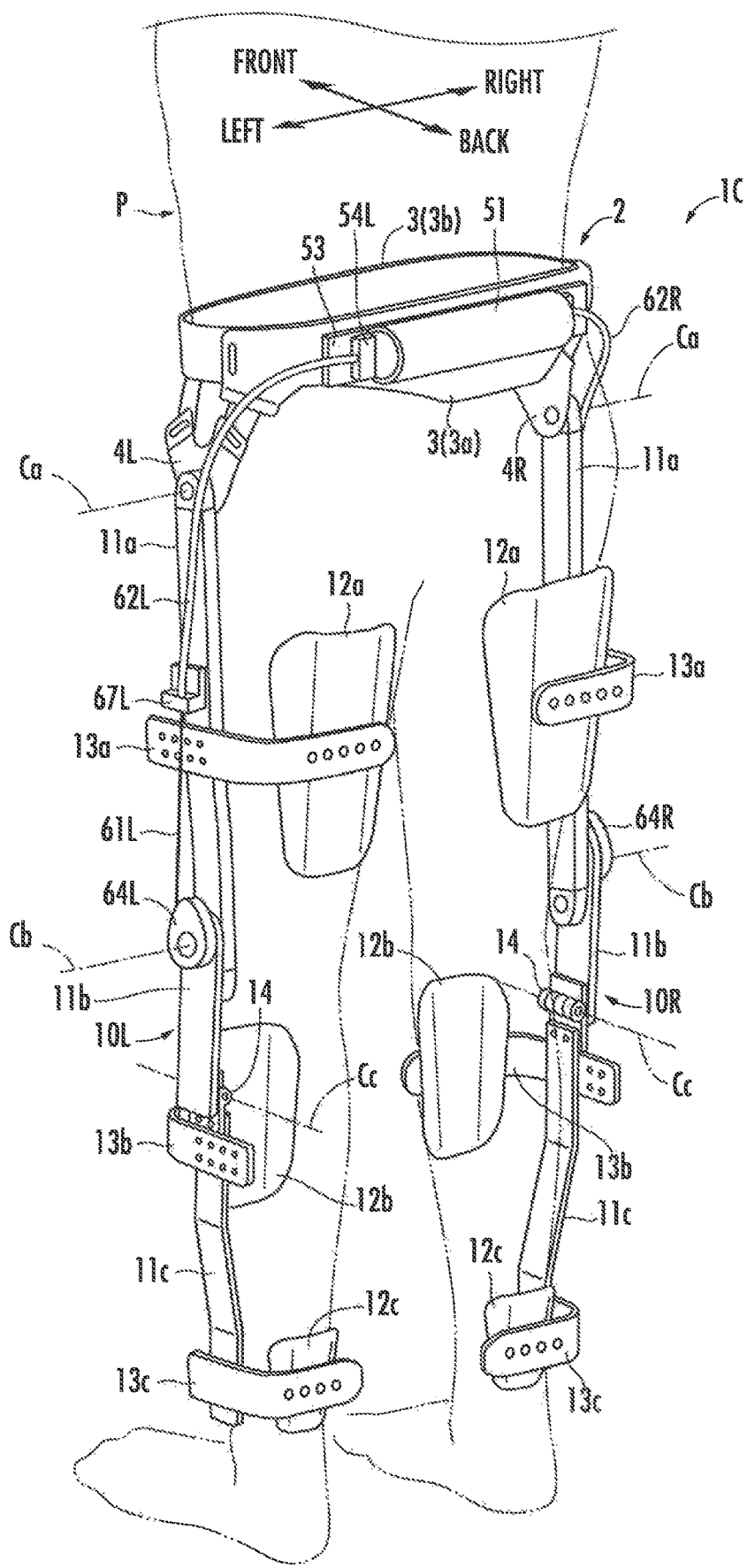
FIG. 7 is a perspective view illustrating an overall structure of a limb motion support device according to a third embodiment (or a fourth embodiment) of the present invention.
Figure 8:
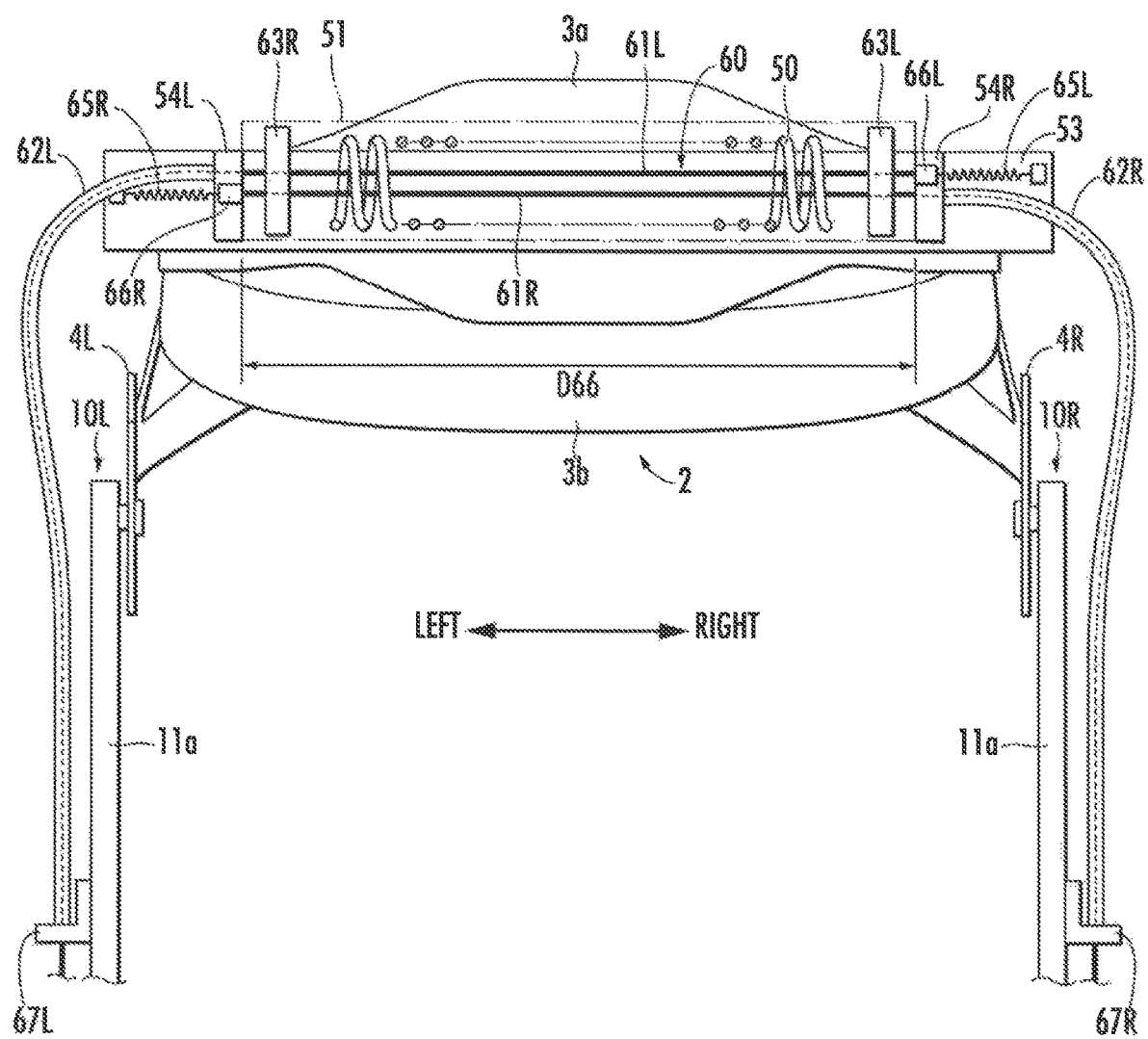
FIG. 8 is a diagram illustrating a main structure (a main structure in a state where both of the right and left limbs (legs) are stretched) of the limb motion support device according to the third embodiment.

Specifically, referring to FIGS. 7 and 8, the motion support device 1C of this embodiment includes a base plate 53 extending in the horizontal direction so as to be provided in a fixed manner to the back of the hip pad member 3a of the body attachment member 2. Moreover, a pair of right and left mounting plates 54R and 54L are provided in a protruding condition so as to protrude to the rear at the right and left ends of the base plate 53.

Additionally, the spring member 50 (illustrated in FIG. 8) is arranged to be housed in a cylindrical guide tube 51 between the mounting plates 54L and 54R. As illustrated in FIG. 8, the guide tube 51 is interposed between the mounting plates 54L and 54R in such a way that the axial direction of the guide tube 51 extends in the horizontal direction. Furthermore, the guide tube 51 is fixed to the base plate 53 (or the mounting plates 54L and 54R).

The spring member 50 is formed of, for example, a coil spring in this embodiment. Moreover, the spring member 50 is slidably housed in the guide tube 51 so as to be able to expand and contract in the axial direction of the guide tube 51 and so as to be movable in the axial direction of the guide tube 51.

In this embodiment, the elastic force generated by the spring member 50 to apply the assisting force to the user P is generated by a compressive deformation of the spring member 50.

Moreover, the spring member 50 may be formed of, for example, a spring member having the same structure as the structure of the spring member 40 described in the second embodiment, instead of the coil spring.

The motion transmission mechanism 60 in this embodiment includes a pair of wires 61L and 61R as flexible long members, outer tubes 62L and 62R slidably partially covering the wires 61L and 61R, respectively, spring support members 63R and 63L arranged between the mounting plates 54L and 54R and the horizontal ends of the spring member 50, respectively, pulleys 64R and 64L mounted on the right and left leg link mechanisms 10R and 10L, respectively, and slack eliminating spring members 65L and 65R for eliminating slack of the wires 61L and 61R, respectively.

In FIG. 7, the slack eliminating spring members 65L and 65R are not illustrated. In addition, in FIG. 8, the spring support member 63L and the slack eliminating spring member 65L are arranged on the right side of the spring member 50. Note that, however, the spring support member 63L and the slack eliminating spring member 65L are related to the motions of the left leg link mechanism 10L and therefore a reference character "L" is appended to each of the spring support member 63L and the slack eliminating spring member 65L. Similarly, the spring support member 63R and the slack eliminating spring member 65R are related to the motions of the right leg link mechanism 10R and therefore a reference "R" is appended to each of the spring support member 63R and the slack eliminating spring member 65R. This is the same as for locking members 66L and 66R described later.

Hereinafter, first, a detailed description will be made on the configuration related to the motion of the left leg link mechanism 10L of the motion transmission mechanism 60.

The spring support member 63L is a member pressed against the right end of the spring member 50 during the compression of the spring member 50 and is formed, for example, in a disc shape. Additionally, the spring support member 63L is arranged inside the guide tube 51 so as to be movable in the axial direction of the guide tube 51 within a range between the right mounting plate 54R and the right-side end of the spring member 50.

The spring support member 63L may be fixed to the right end of the spring member 50.

The outer tube 62L is disposed in an arbitrarily curved path between a left mounting plate 54L and a mounting plate 67L provided in a protruding condition in the first link 11a so as to protrude on the lateral side of the first link 11a of the leg link mechanism 10L. Both ends of the outer tube 62L are fixed to the mounting plates 54L and 67L, respectively. In the description below, the end on the mounting plate 54L side of the outer tube 62L is referred to as "upper-side end" and the end on the mounting plate 67L side is referred to as "lower-side end."

The wire 61L is slidably inserted into the outer tube 62L and is led out from both ends of the outer tube 62L.

In this case, the portion of the wire 61L led out from the upper-side end of the outer tube 62L slidably passes through the mounting plate 54L and is introduced into the inside of the guide tube 51. Furthermore, the wire 61L slidably passes through the spring support members 63R and 63L in such a way as to extend in the axial direction of the guide tube 52. Then, the wire 61L is led out to the right side of the spring support member 63L. In addition, the wire 61L is disposed passing through the inside space of the spring member 50 between the spring support members 63R and 63L.

Furthermore, the locking member 66L is fixed to the distal end of the wire 61L led out to the right side of the spring support member 63L. The locking member 66L has a larger diameter than the diameter of the insertion hole (not illustrated) for the wire 61L in the spring support member 63L.

The distal end of the wire 61L or the locking member 66L may be fixed to the spring support member 63L.

Moreover, a slack eliminating spring member 65L is connected to the distal end of the wire 61L via the locking member 66L. The slack eliminating spring member 65L has sufficiently smaller rigidity (spring constant) than the rigidity of the spring member 50. The slack eliminating spring member 65L is formed of, for example, a coil spring in this embodiment. The slack eliminating spring member 65L, however, may be formed of a spring member other than the coil spring, such as, for example, a rubber strap or other long rubber member.

Furthermore, the slack eliminating spring member 65L is connected at one end to the distal end of the wire 61L via the locking member 66L so as to be able to expand and contract with the running of the wire 61L in the axial direction of the guide tube 51. Moreover, the slack eliminating spring member 65L is connected at the other end to the base plate 53.

The portion of the wire 61L led out from the lower-side end of the outer tube 62L slidably passes through the mounting plate 67L and then is wrapped around the outer periphery of the pulley 64L.

The aforementioned pulley 64L is mounted on the second link 11b so as to be rotatable around the swing axis Cb of the second link 11b integrally with the second link 11b of the left leg link mechanism 10L.

Therefore, when the left leg of the user P is bent so that the bending degree at the knee increases, the wire 61L is wound on the pulley 64L, thereby increasing the path length of the portion of the wire 61L led out from the lower-side end of the outer tube 62L.

This pulley 64L has an outer periphery formed in an eccentric cam shape in this embodiment. In this case, the outer peripheral shape of the pulley 64L is formed so as to increase the distance from the center of rotation (the swing axis Cb) of the pulley 64L to the tangent of the wire 61L in contact with the outer periphery of the pulley 64L (the distance is so-called a moment arm length) with an increase in the bending degree of the leg (the bending degree at the knee), in the case of bending the left leg of the user P equipped with the motion support device 1C from a stretched state.

In this embodiment, the mechanism related to the motion of the left leg link mechanism 10L of the motion transmission mechanism 60 is configured as described above. The same applies to the mechanism related to the motion of the right leg link mechanism 10R. In this case, the mechanism on the right leg link mechanism 10R side of the motion transmission mechanism 60 can be described by replacing "left," "right," "L," and "R" in the above description on the mechanism related to the motion of the left leg link mechanism 10L of the motion transmission mechanism 60 with "right," "left," "R," and "L," respectively.

In this embodiment, each of the locking members 66L and 66R corresponds to the fifth member of the present invention.

More specifically, in this embodiment, the arranged positions of the locking members 66L and 66R are set so that the distance between the locking members 66L and 66R in the axial direction of the guide tube 51 (specifically, the distance between the end face of the locking member 66L on the spring support member 63L side and the end face of the locking member 66R on the spring support member 63R side; hereinafter, the distance is referred to as "locking member distance D66") is longer than the length (a length of a predetermined value) obtained by adding the length of the spring member 50 in a natural length state to the thicknesses of the spring members 63L and 63R as illustrated in FIG. 8, in a state where the legs of the user P equipped with the motion support device 1C are both stretched (a state in which both of the leg link mechanisms 10L and 10R are stretched).

Therefore, in the state where both legs of the user P are stretched, the spring member 50 is movable in the axial direction of the guide tube 51 in the natural length state (without being compressed).

Subsequently, the working of the motion support device 1C configured as described above will be described. First, such a case is assumed that the user P equipped with the motion support device 1C bends the legs at the knees at the same bending degree from a state in which the legs are stretched (for example, when the user P sits in a chair or the like or squats or the like).

In this case, the right and left wires 61R and 61L run in the winding direction around the pulleys 64R and 64L, respectively, with an increase in the bending degrees of the legs of the user P (the bending degree at both knees and the bending degree at both hip joints). Therefore, both of the locking members 66L and 66R move so as to come close to each other in the axial direction of the guide tube 51. In other words, the locking member distance D66 decreases with an increase in the bending degrees of the legs of the user P.

At this time, the spring support members 63L and 63R are not pressed against the left-side end and the right-side end of the spring member 50, respectively, until the locking member distance D66 reaches the length of the predetermined value obtained by adding the length of the spring member 50 in the natural length state to the thicknesses of the spring members 63L and 63R. Therefore, the spring member 50 does not generate an elastic force. In this situation, the tensions of the wires 61L and 61R are kept sufficiently small by the slack eliminating spring members 65L and 65R, respectively.

Therefore, the torques generated by the tensions of the wires 61L and 61R substantially do not act on the pulleys 64L and 64R, respectively. Consequently, the assisting forces in the direction of stretching the legs of the user P substantially are not generated (the assisting forces are sufficiently small).

If the bending degrees of the legs of the user P further increase, the locking member distance D66 decreases to the length of the predetermined value obtained by adding the length of the spring member 50 in the natural length state to the thicknesses of the spring members 63L and 63R.

Figure 9:
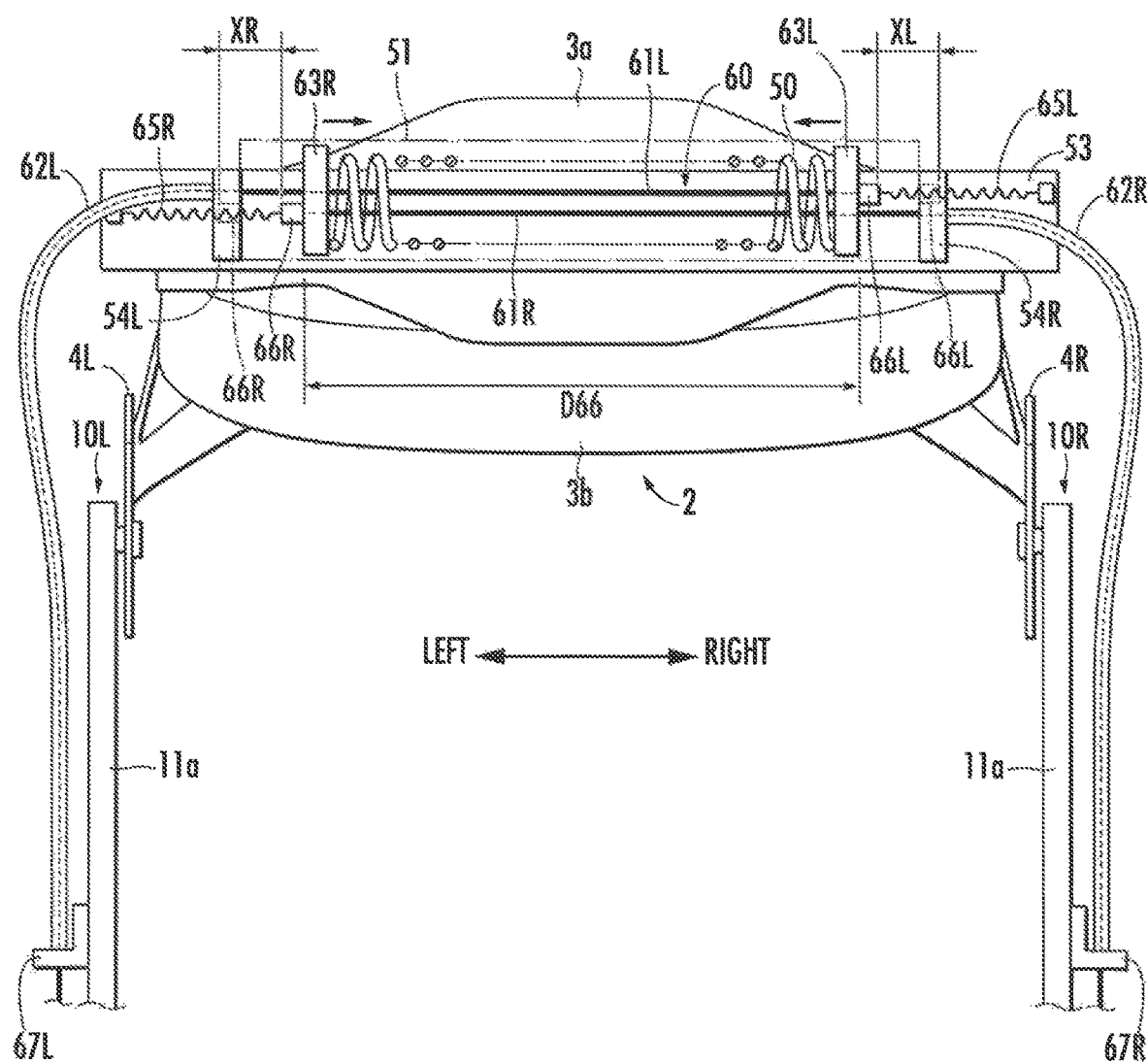
FIG. 9 is a diagram illustrating a main structure (a main structure in a state where both of the right and left limbs (legs) are bent) of the limb motion support device according to the third embodiment.

Accordingly, as illustrated in FIG. 9, the spring support member 63L comes in contact with the right-side end of the spring member 50 with being sandwiched between the right-side end of the spring member 50 and the locking member 66L. Moreover, the spring support member 63R comes in contact with the left-side end of the spring member 50 with being sandwiched between the left-side end of the spring member 50 and the locking member 66R. Thereby, the locking members 66L and 66R are bound to the respective ends of the spring member 50. Hereinafter, this state is referred to as "spring member compressible state."

In this situation, the distance between the spring support members 63R and 63L decreases with an increase in the bending degrees of the legs of the user P. Therefore, the spring member 50 is compressed, thereby generating and increasing an elastic force. Consequently, the tensions of the wires 61L and 61R increase. Therefore, torques respectively acting on the pulleys 64L and 64R (respective torques in the stretching direction of the leg link mechanisms 10L and 10R) increase. Thereby, assisting forces in the stretching direction act on the legs of the user P. Furthermore, the assisting forces increase with an increase in the bending degrees of the legs of the user P.

In the case of bending both legs of the user P in this manner, the elastic force of the spring member 50 is not generated until the bending degrees of the legs reach a predetermined bending degree (the bending degree at which the spring member compressible state starts). Therefore, assisting forces substantially do not act on the legs of the user P.

Thereafter, when the bending degrees of the legs of the user P exceed the predetermined bending degree, the elastic force of the spring member 50 is generated and the tension of each of the wires 61L and 61R increases. Consequently, assisting forces in the stretching direction act on both legs of the user P.

Subsequently, such a case is assumed that the user P equipped with the motion support device 1C maintains one leg such as, for example, the right leg in the stretched state (or a state close thereto) while bending the other leg (the left leg in this specification).

In this case, only the wire 61L of the right and left wires 61R and 61L runs in the winding direction around the pulley 64L with an increase in the bending degree of the left leg (the bending degree at the knee) of the user P. Therefore, the locking member 66L moves in the direction of coming close to the locking member 66R in the axial direction of the guide tube 51 in a state where the locking member 66R does not move in the axial direction of the guide tube 51 (or a state where the locking member 66R does not move almost at all). Thereby, the locking member distance D66 decreases.

At this time, similarly to the case of bending both legs of the user P, the spring member 50 does not generate an elastic force until the locking member distance D66 reaches the length of the predetermined value obtained by adding the length of the spring member 50 in the natural length state to the thicknesses of the spring members 63L and 63R. Consequently, the respective tensions of the wires 61L and 61R are kept sufficiently small by the slack eliminating spring members 65L and 65R, respectively. Accordingly, the assisting forces in a direction of stretching the legs of the user P are substantially not generated (the assisting forces are sufficiently small).

Figure 10:
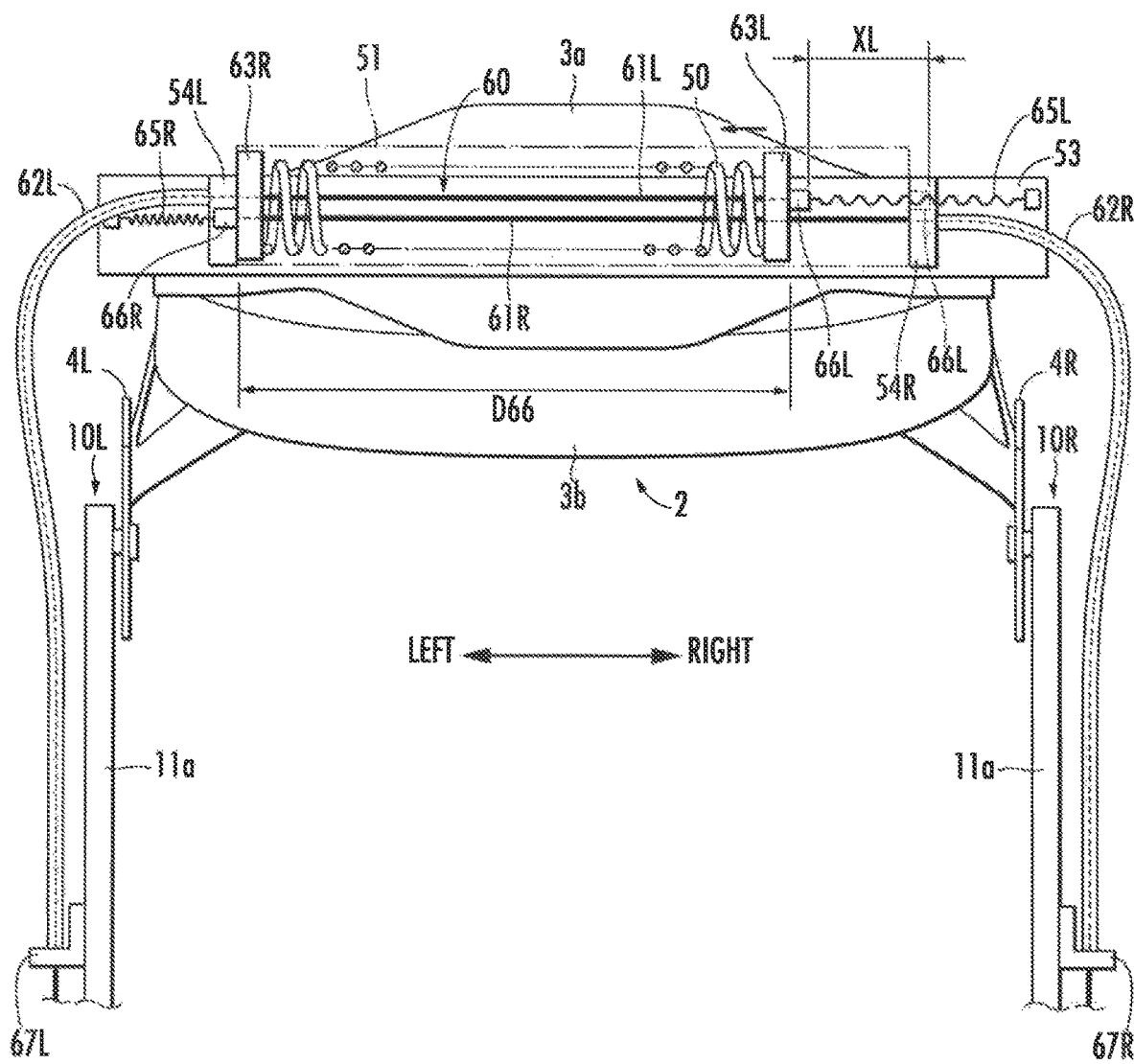
FIG. 10 is a diagram illustrating a main structure (a main structure in a state where a left limb (leg) is bent) of the limb motion support device according to the third embodiment.

If the bending degree of the left leg of the user P further increases, the locking member distance D66 decreases to the length of the predetermined value obtained by adding the length of the spring member 50 in the natural length state to the thicknesses of the spring members 63L and 63R. Therefore, as illustrated in FIG. 10, the positional relationship between the spring member 50, the spring support members 63L and 63R, and the locking members 66L and 66R is placed in the spring member compressible state.

In this case, however, the right leg of the user P is placed in the stretched state (or a state close thereto). Therefore, the spring member 50, the spring support members 63L and 63R, and the locking members 66L and 66R are placed in a state in which the entirety thereof has been moved to the left end side of the guide tube 51.

Therefore, the bending angle of the left leg at which the spring member compressible state starts is larger than the bending angle of both legs at which the spring member compressible state starts in the case of bending both legs.

Hereinafter, the spring member 50 is compressed with an increase in the bending degree of the left leg of the user P, thereby increasing the elastic force. Consequently, the tension of the wire 61L increases and therefore a torque acting on the pulley 64L (a torque of the leg link mechanism 10L in the stretching direction) increases. Thereby, an assisting force in the stretching direction acts on the left leg of the user P.

In addition, although the tension of the right wire 61R also increases, the right leg link mechanism 10R is placed in the stretched state or in a state close thereto. Furthermore, the moment arm length of the pulley 64R is small. Therefore, the assisting force in the direction of changing the bending degree of the right leg of the user P is smaller than in the case of the left leg.

The above working also applies to a case of bending the right leg of the user P while keeping the left leg thereof in the stretched state (or a state close thereto).

As described above, in both cases of bending both legs of the user P and bending only one leg thereof, the assisting forces to both legs of the user P are substantially not generated until the bending degrees of the legs or the bending degree of one leg reaches a certain bending degree (the bending degree at which the spring member compressible state starts). Thereafter, when the bending degrees of the legs or the bending degree of one leg of the user P exceeds the bending degree at which the spring member compressible state starts, the assisting forces or force in the stretching direction acts on the legs or one leg of the user P.

In this case, regarding the bending degree at which the assisting forces or force in the stretching direction starts to act on the legs or one leg of the user P (the bending degree at which the spring member compressible state starts), the bending degree in the case of bending one leg of the user P is larger than the bending degree in the case of bending both legs of the user P.

Figure 11:
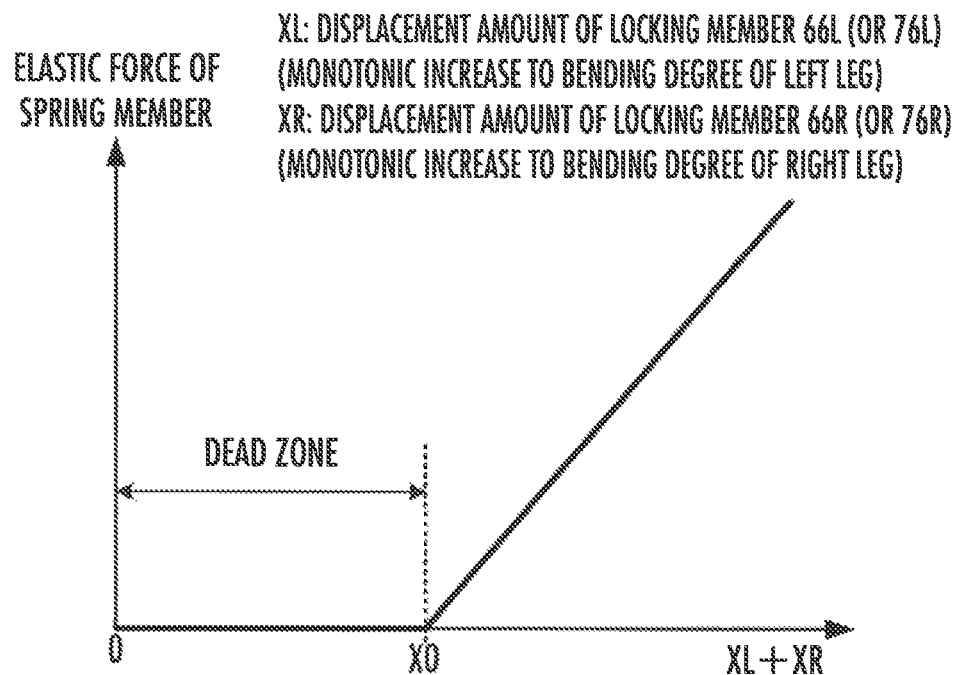
FIG. 11 is a diagram illustrating variation characteristics of an elastic force of a spring member of the limb motion support device according to the third embodiment (or the fourth embodiment)

Due to the working as described above, the elastic force of the spring member 50 basically changes in the pattern as illustrated in the graph of FIG. 11.

Note that XL indicates a displacement amount of the locking member 66L (a displacement amount associated with an increase in the bending degree from the stretched state of the left leg of the user P) and XR indicates a displacement amount of the locking member 66R (a displacement amount associated with an increase in the bending degree from the stretched state of the right leg of the user P).

Moreover, X0 indicates a value obtained by subtracting a length of a predetermined value, which is obtained by adding the length of the spring member 50 in the natural length state to the thicknesses of the spring members 63L and 63R, from the locking member distance D66 in the stretched state of both legs of the user P (in the stretched state of the leg link mechanisms 10L and 10R). In other words, X0 is a value of XL+XR at the start of the spring member compressible state.

In FIG. 11, a state satisfying an inequality "XL+XR<X0" means a state in which the spring member 50 is not compressed and the elastic force of the spring member 50 is not generated. Therefore, a range in which the bending degrees of the legs of the user P satisfy the inequality "XL+XR<X0" is a dead zone in which the respective assisting forces substantially do not act on the legs of the user P.

Furthermore, a state satisfying an inequality "XL+XR≥X0" is a state in which the positional relationship between the spring member 50, the spring support members 63L and 63R, and the locking members 66L and 66R is placed in the spring member compressible state. In this state, the elastic force of the spring member 50 increases with an increase in the bending degree of each of the legs of the user P (consequently, with an increase in the value of XL+XR).

Then, in the case of keeping one leg (supporting leg) in the stretched state or in a state close thereto with the other leg (free leg) bent as in walking of the user P, "XL+XR≈XL" or "XL+XR≈XL" is satisfied. Therefore, "XL+XR=X0" is satisfied and the bending degree of the other leg at which the elastic force of the spring member 50 starts to be generated is relatively large.

As described above, regarding the bending of each leg at the hip joint (the bending to the body) in walking of the user P, one leg is bent at the hip joint while the other leg moves so as to be stretched at the hip joint. Therefore, changes in the path lengths of the wires 61L and 61R, which are caused by the bending of the legs at the hip joints, are counteracted. Accordingly, the value of "XL+XR" can be easily relatively small.

On the other hand, when the user P bends the legs at the same bending degree such as a case of sitting in a chair or the like or squatting, "XL+XR≈2×XL (≈2×XR)" is satisfied. Accordingly, the equation "XL+XR=X0" is satisfied and the bending degrees of the legs at which the elastic force of the spring member 50 starts to be generated are smaller than in the case of bending only one leg.

Therefore, the distance X0 of the predetermined value is able to be set so that the value of "XL+XR" is within the range expressed by "XL+XR<X0" as much as possible (accordingly, the elastic force of the spring member 50 is not generated), for example, during walking of the user P. This prevents the assisting forces from acting on the legs of the user P during walking. Consequently, the user P is able to walk in much the same way as in the normal walking without feeling uncomfortable.

Moreover, when the user P bends the legs at the same bending degree such as a case of sitting in a chair or the like or squatting, the distance X0 of the predetermined value is able to be set so that the value of "XL+XR" satisfies "XL+XR≥X0" from a state of the bending degree in the middle of bending both legs. This enables assisting forces in the stretching direction to act on the legs of the user P when the user P sits in a chair or the like or squats. Therefore, the user P is able to easily stand up from a sitting state or a squatting state.

Furthermore, the motion support device 1C has a light-weight and simple configuration similarly to the configuration of the first embodiment. Therefore, the user P equipped with the motion support device 1C is able to perform the walking motion or the like in the same manner as in the normal, without feeling uncomfortable or burdened.

Fourth Embodiment

Subsequently, a fourth embodiment of the present invention will be described with reference to FIGS. 12 to 14. In a limb motion support device 1D of this embodiment, the configurations of the body attachment member 2 and the leg link mechanisms 10L and 10R are the same as those of the third embodiment and each include a lot of constituent elements in common with those of the third embodiment. Therefore, in this embodiment, the differences from the third embodiment are mainly described and the description of the same matters as the third embodiment is omitted.

The motion support device 1C of the third embodiment is configured to generate elastic forces for applying assisting forces to the user P by the compressive deformation of the spring member 50. Meanwhile, the limb motion support device 1D (hereinafter, simply referred to as "motion support device 1D") of this embodiment is configured to generate the elastic force by an extension (tensile deformation) of the spring member 50.

Figure 12:
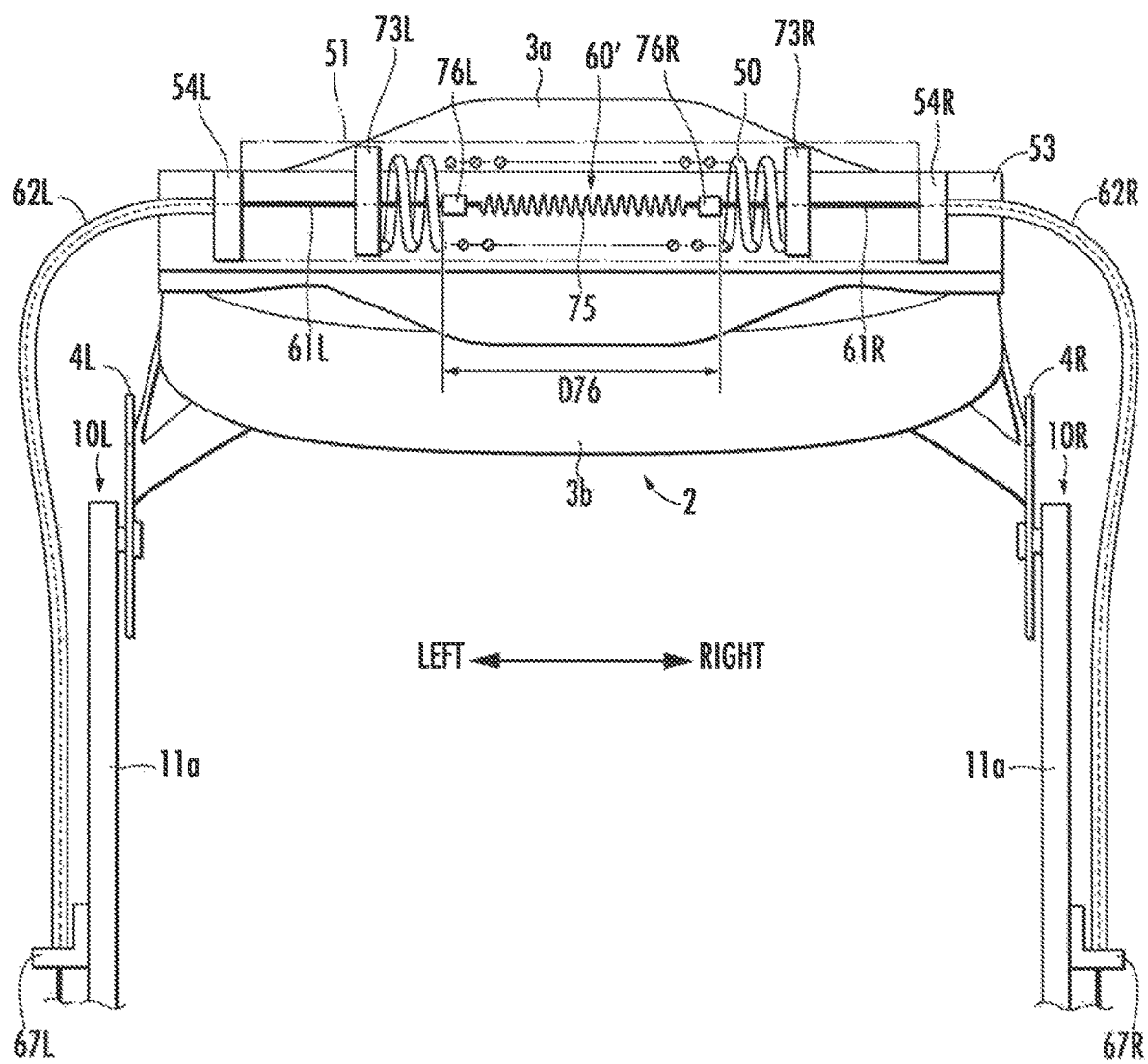
FIG. 12 is a diagram illustrating a main structure (a main structure in a state where both of the right and left limbs (legs) are stretched) of the limb motion support device according to the fourth embodiment.

Specifically, referring to FIG. 12, a base plate 53, mounting plates 54L and 54R, a guide tube 51, and a spring member 50 (coil spring) are installed in a hip pad member 3a of a body attachment member 2, similarly to the third embodiment, in the motion support device 1D of this embodiment.

On the other hand, the motion support device 1D of this embodiment includes a motion transmission mechanism 60' different in a part of the configuration from the configuration of the third embodiment, as a motion transmission mechanism for transmitting the bending and stretching motion of the legs of the user P to the spring member 50.

Similarly to the third embodiment, the motion transmission mechanism 60' includes a pair of wires 61L and 61R, outer tubes 62L and 62R into which the wires 61L and 61R are inserted, respectively, and pulleys 64L and 64R with the wires 61L and 61R wrapped therearound, where the wires 61L and 61R are led out from the lower-side ends of the outer tubes 62L and 62R, respectively.

Meanwhile, the motion transmission mechanism 60' includes plate-like spring support members 73L and 73R, which are bonded to the left-side end and the right-side end of the spring member 50, respectively, instead of the spring support members 63L and 63R in the third embodiment. Furthermore, the motion transmission mechanism 60' includes a single slack eliminating spring member 75 which is housed in the guide tube 51, instead of the slack eliminating spring members 65L and 65R in the third embodiment.

In this embodiment, a portion of the wire 61L led out from the upper-side end of the outer tube 62L slidably passes through the mounting plate 54L and is introduced into the guide tube 51, in the same manner as in the third embodiment. Similarly, a portion of the wire 61R led out from the upper-side end of the outer tube 62R slidably passes through the mounting plate 54R and is introduced into the guide tube 51.

In this embodiment, however, the left wire 61L introduced into the guide tube 51 slidably passes through the spring support member 70L bonded to the left-side end of the spring member 50. Furthermore, the wire 61L is extended in the axial direction of the guide tube 51 up to the position inside the spring member 50. Similarly, the right wire 61R introduced into the guide tube 51 slidably passes through the spring support member 70R bonded to the right-side end of the spring member 50. Furthermore, the wire 61R is extended in the axial direction of the guide tube 51 up to the position inside the spring member 50.

In addition, locking members 76L and 76R each having a larger diameter than the diameter of the insertion holes (not illustrated) of the wires 61L and 61R in the spring support members 73L and 73R are fixed to the distal ends of the wires 61L and 61R, respectively. Therefore, the locking members 76L and 76R are located inside the spring member 50 in this embodiment.

Moreover, the distal ends of the wires 61L and 61R are connected to each other via the slack eliminating spring member 75. The slack eliminating spring member 75 has sufficiently smaller rigidity (spring constant) than the rigidity of the spring member 50. The slack eliminating spring member 75 is formed of, for example, a coil spring in this embodiment. The slack eliminating spring member 75, however, may be formed of a spring member other than the coil spring, such as, for example, a rubber strap or other long rubber member.

The slack eliminating spring member 75 is arranged inside the spring member 50 so as to be able to expand and contract in almost the same direction as the axial direction of the guide tube 51. Furthermore, the left-side end of the slack eliminating spring member 75 is connected to the distal end of the wire 61L via the locking member 76L. Moreover, the right-side end of the slack eliminating spring member 75 is connected to the distal end of the wire 61R via the locking member 76R.

More specifically, in this embodiment, the arranged positions of the locking members 76L and 76R are set so that the distance between the locking members 76L and 76R in the axial direction of the guide tube 51 (specifically, the distance between the end face of the locking member 76L on the spring support member 73L side and the end face of the locking member 76R on the spring support member 73R side: hereinafter, the distance is referred to as "locking member distance D76") is shorter than the length of the spring member 50 in a natural length state (=the distance between the spring support members 73L and 73R), in a state where the legs of the user P equipped with the motion support device 1D are both stretched (the state in which both of the leg link mechanisms 10L and 10R are stretched).

Therefore, in the state where both legs of the user P are stretched, the spring member 50 is movable in the axial direction of the guide tube 51 in the natural length state (without being compressed).

In this embodiment, each of the locking members 76L and 76R corresponds to the fifth member of the present invention.

The motion support device 1D of this embodiment is the same as the motion support device 1C of the third embodiment except for the matters described above.

Subsequently, the working of the motion support device 1D of this embodiment will be described. First, such a case is assumed that the user P equipped with the motion support device 1D bends both legs at the same bending degree from a state in which the legs are stretched (for example, when the user P sits in a chair or the like or squats or the like).

In this case, the right and left wires 61R and 61L run in the winding direction around the pulleys 64R and 64L, respectively, with an increase in the bending degrees of the legs (the bending degrees at the knees) of the user P. Therefore, both of the locking members 76L and 76R move so as to separate from each other in the axial direction of the guide tube 51. In other words, the locking member distance D76 increases with an increase in the bending degrees of the legs of the user P.

At this time, until the locking member distance D76 reaches a predetermined value that matches the length of the spring member 50 in the natural length state (the distance between the spring support members 73L and 73R), the locking members 76L and 76R are not placed in contact with the spring support members 73L and 73R, respectively. Therefore, the spring member 50 does not generate an elastic force. In this situation, the tensions of the wires 61L and 61R are kept to be sufficiently small by the slack eliminating spring member 75.

Therefore, the torques generated by the tensions of the wires 61L and 61R substantially do not act on the pulleys 64L and 64R, respectively. Consequently, the assisting forces in the direction of stretching the legs of the user P substantially are not generated (the assisting forces are sufficiently small).

If the bending degrees of the legs of the user P further increase, the locking member distance D76 increases with time, up to a predetermined value that matches the length of the spring member 50 in the natural length state.

Figure 13:
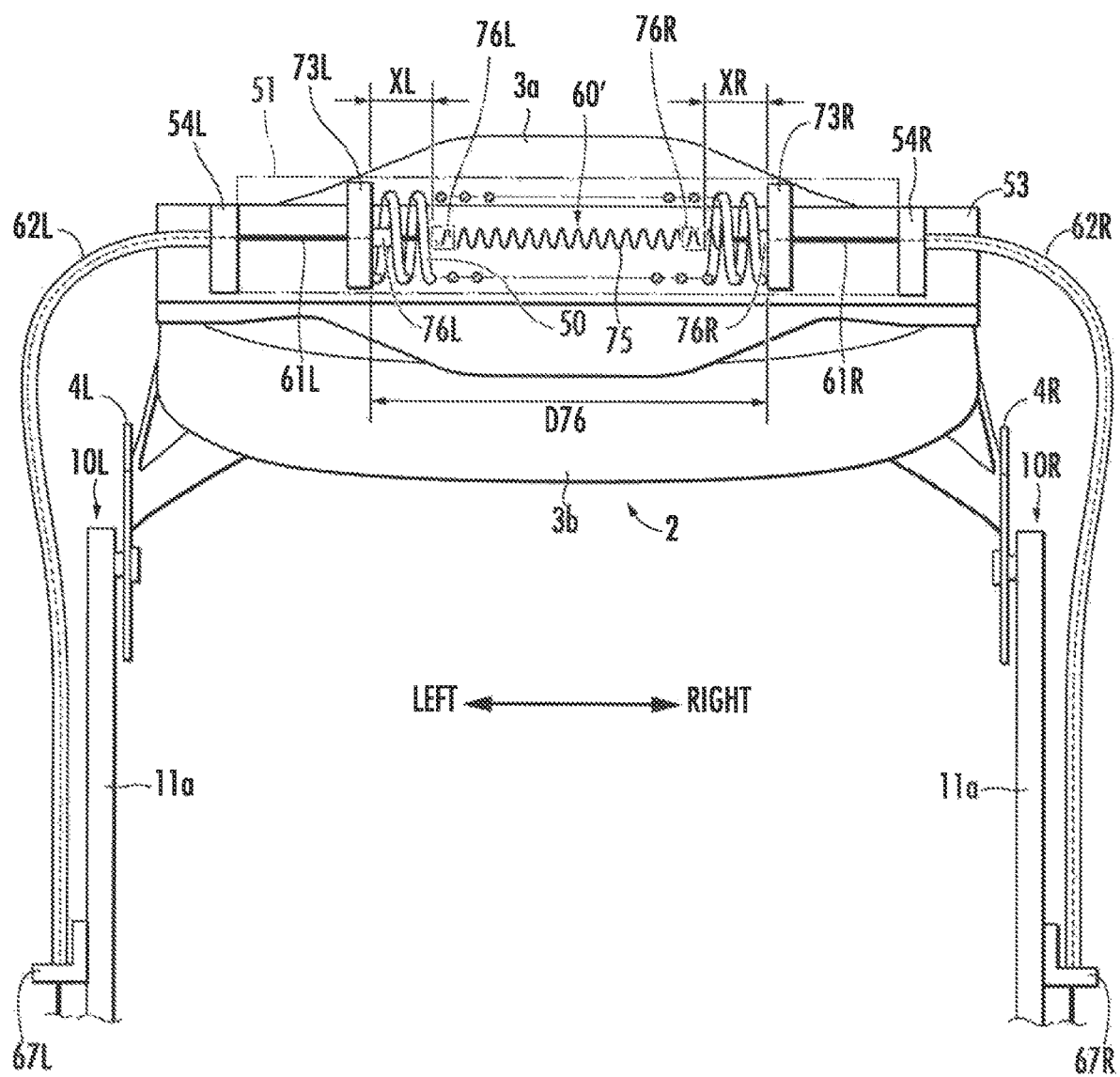
FIG. 13 is a diagram illustrating a main structure (a main structure in a state where both of the right and left limbs (legs) are bent) of the limb motion support device according to the fourth embodiment.
Figure 14:
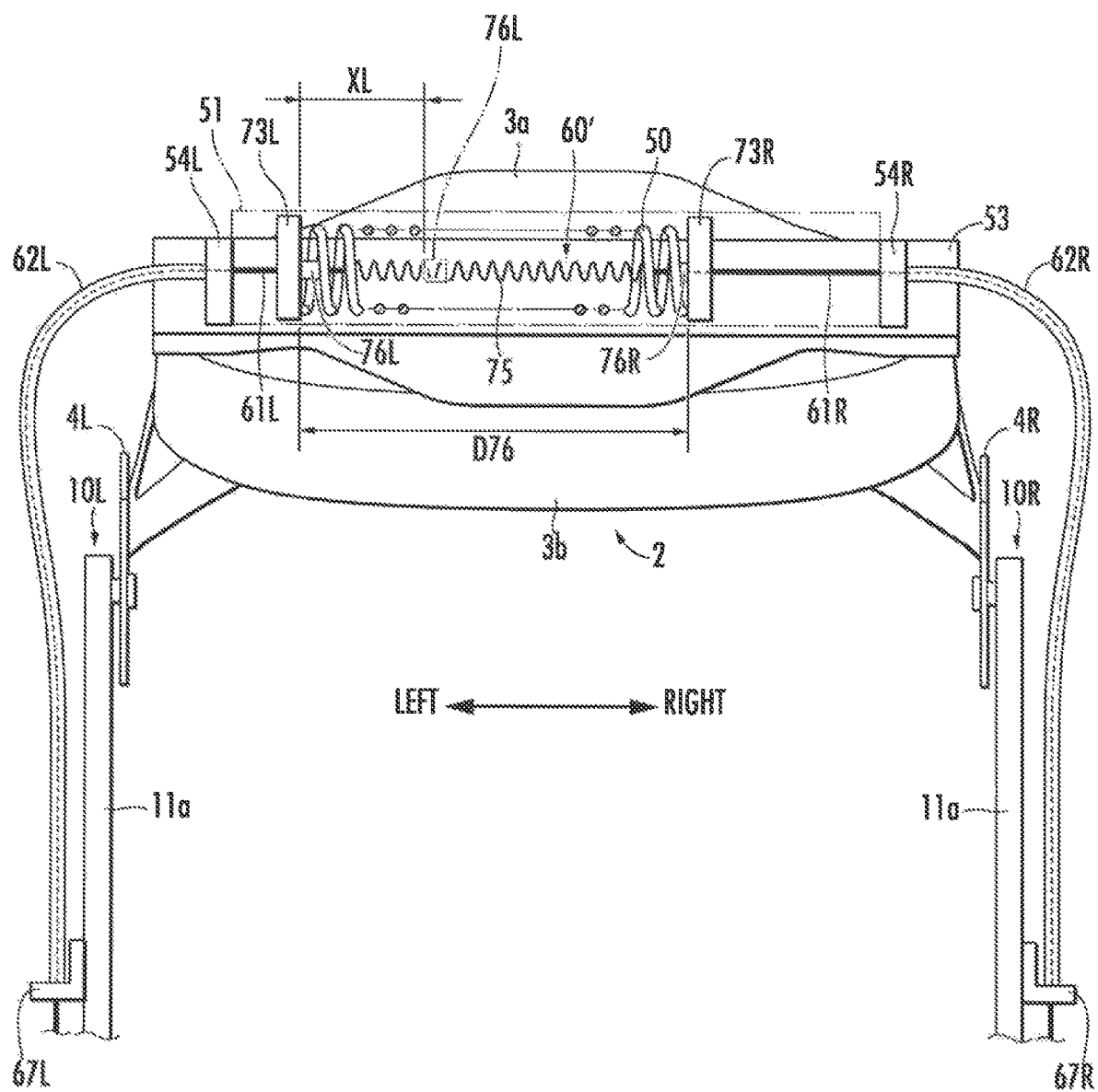
FIG. 14 is a diagram illustrating a main structure (a main structure in a state where a left limb (leg) is bent) of the limb motion support device according to the third embodiment.

Accordingly, as illustrated in FIG. 13, the locking members 76L and 76R are placed in contact with the spring support members 73L and 73R, respectively. Hereinafter, this state is referred to as "spring member extendible state."

In this situation, the spring member 50 is extended to generate an elastic force and the elastic force increases due to an increase in the locking member distance D76 associated with an increase in the bending degrees of the legs of the user P. Consequently, the tensions of the wires 61L and 61R increase. Therefore, torques respectively acting on the pulleys 64L and 64R (respective torques in the stretching direction of the leg link mechanisms 10L and 10R) increase. Thereby, assisting forces in the stretching direction act on the legs of the user P. Furthermore, the assisting forces increase with an increase in the bending degrees of the legs of the user P.

In the case of bending both legs of the user P in this manner, the elastic force of the spring member 50 is not generated until the bending degrees of the legs reach the predetermined bending degree (the bending degree at which the spring member extensible state starts). Therefore, assisting forces substantially do not act on the legs of the user P.

Thereafter, when the bending degrees of the legs of the user P exceed the predetermined bending degree, the elastic force of the spring member 50 is generated. Therefore, the tension of each of the wires 61L and 61R increases. Consequently, assisting forces in the stretching direction act on both legs of the user P.

Subsequently, such a case is assumed that the user P equipped with the motion support device 1C maintains one leg such as, for example, the right leg in the stretched state (or a state close thereto) while bending the other leg (the left leg in this specification) (for example, a case that the user P is walking).

In this case, only the wire 61L of the right and left wires 61R and 61L runs in the winding direction around the pulley 64L with an increase in the bending degree of the left leg (the bending degree at the knee) of the user P. Therefore, the locking member 76L moves in the direction of separating from the locking member 76R in the axial direction of the guide tube 51 in a state where the locking member 76R does not move in the axial direction of the guide tube 51 (or does not move almost at all). Thereby, the locking member distance D76 increases.

At this time, similarly to the case of bending both legs of the user P, the spring member 50 does not generate an elastic force until the locking member distance D76 reaches the predetermined value that matches the length of the spring member 50 in the natural length state. Consequently, the tensions of the wires 61L and 61R are kept sufficiently small by the slack eliminating spring member 75.

Accordingly, the assisting forces in a direction of stretching the legs of the user P are substantially not generated (the assisting forces are sufficiently small).

If the bending degree of the left leg of the user P further increases, the locking member distance D76 increases to the predetermined value matching the length of the spring member 50 in the natural length state. Therefore, as illustrated in FIG. 14, the positional relationship between the spring member 50, the spring support members 73L and 73R, and the locking members 76L and 76R is placed in the spring member extendible state.

In this case, however, the right leg of the user P is placed in the stretched state (or a state close thereto). Therefore, the spring member 50, the spring support members 73L and 73R, and the locking members 76L and 76R are placed in a state in which the entirety thereof has been moved to the left end side of the guide tube 51.

Therefore, the bending angle of the left leg at which the spring member extendible state starts is larger than the bending angle of both legs at which the spring member extendible state starts in the case of bending both legs.

Hereinafter, the spring member 50 is extended with an increase in the bending degree of the left leg of the user P, thereby increasing the elastic force. Consequently, the tension of the wire 61L increases. Therefore, the torque acting on the pulley 64L (the torque of the leg link mechanism 10L in the stretching direction) increases. Thereby, an assisting force in the stretching direction acts on the left leg of the user P.

In addition, the right leg link mechanism 10R is placed in the stretched state or in a state close thereto. Furthermore, the moment arm length of the pulley 64R is small. Therefore, the assisting force in the direction of changing the bending degree of the right leg of the user P substantially does not act on the right leg of the user P in the stretched state.

The above working also applies to a case of bending the right leg while keeping the left leg of the user P in the stretched state (or a state close thereto).

As described above, in both cases of bending both legs of the user P and bending only one leg, the assisting forces to both legs of the user P are substantially not generated until the bending degrees of both legs or the bending degree of one leg reaches a certain bending degree (the bending degree at which the spring member extendible state starts). Thereafter, when the bending degrees of both legs or the bending degree of one leg of the user P exceeds the bending degree at which the spring member extendible state starts, the assisting forces or force in the stretching direction acts on the legs or one leg of the user P.

In this case, regarding the bending degree at which the assisting forces or force in the stretching direction starts to act on the legs or one leg of the user P (the bending degree at which the spring member compressible state starts), the bending degree in the case of bending one leg of the user P is larger than the bending degree in the case of bending both legs of the user P.

Also in this embodiment, the relationship between the total sum (=XL+XR) of a displacement amount of the locking member 76L (a displacement amount associated with an increase in the bending degree from the stretched state of the left leg of the user P) XL and a displacement amount of the locking member 76R (a displacement amount associated with an increase in the bending degree from the stretched state of the right leg of the user P) XR (=XL+XR) and the elastic force generated by the spring member 50 is as illustrated in FIG. 11, similarly to the third embodiment. In this embodiment, X0 indicates a value (predetermined value) obtained by subtracting the locking member distance D76 in the state of stretching both legs of the user P (the state of stretching both leg link mechanisms 10L and 10R) from the length of the spring member 50 in the natural length state (the distance between the spring support members 73L and 73R).

Additionally, the predetermined value X0 is preset in the same manner as the third embodiment, thereby achieving the same advantageous effects as in the third embodiment.

Furthermore, the motion support device 1D has a lightweight and simple configuration similarly to the configuration of the first embodiment. Therefore, the user P equipped with the motion support device 1D is able to perform the walking motion or the like in the same manner as in the normal, without feeling uncomfortable or burdened.

Other Embodiments

The present invention is not limited to the above-described embodiments. Other some embodiments will be described hereinbelow. For example, the motion support device 1A according to the first embodiment or the motion support device 1B according to the second embodiment may include a control mechanism (a mechanism corresponding to the first bending degree control mechanism of the present invention) for enabling an appropriate change in the bending degrees of both legs at which the elastic forces of the spring members 20L and 20R or 40L and 40R start to be substantially generated in the case of bending both legs of the user P. As the first bending degree control mechanism, for example, a mechanism for enabling an appropriate change (hereinafter, referred to as "path length control mechanism") in the path length of a part of the wire 31 may be employed.

Figure 15:
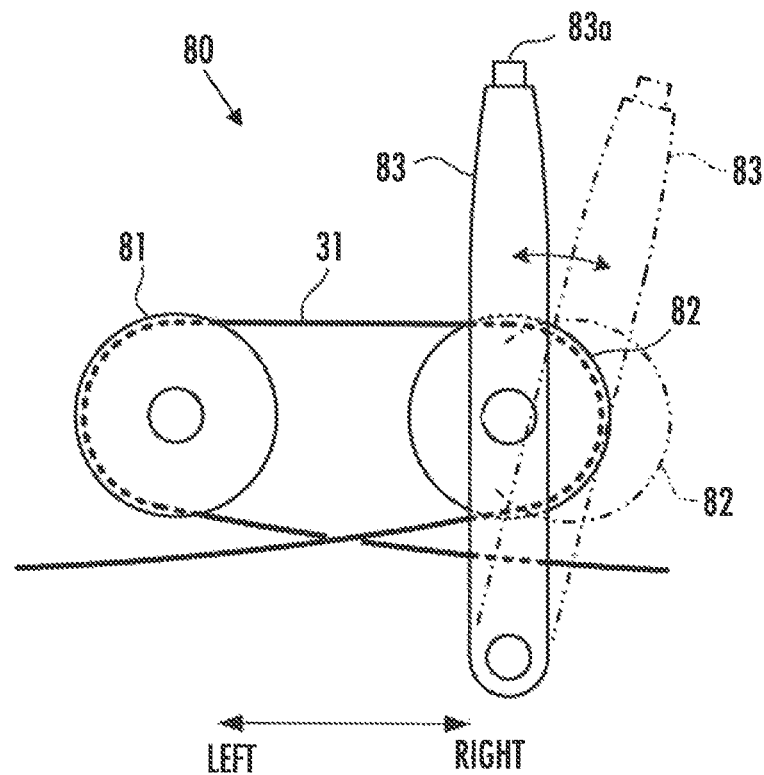
FIG. 15 is a diagram illustrating a first example of a path length control mechanism.
Figure 16:
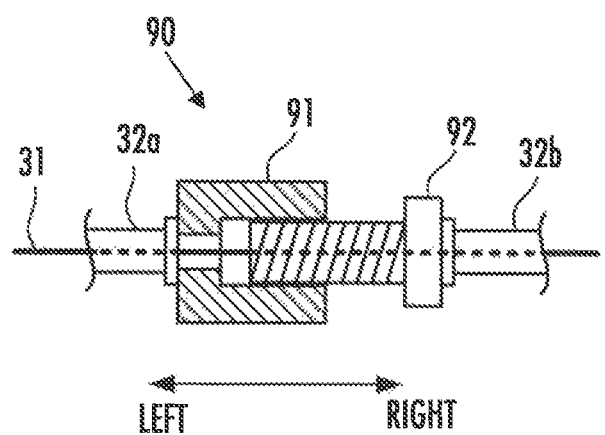
FIG. 16 is a diagram illustrating a second example of the path length control mechanism.

For example, in the motion support device 1A or 1B, a path length control mechanism 80 or 90 having the structure as illustrated in FIG. 15 or 16 may be interposed in the middle of the path of the wire 31 on the back side of the hip pad member 3a of the body attachment member 2.

The path length control mechanism 80 illustrated in FIG. 15 includes a pair of pulleys 81 and 82 juxtaposed in the horizontal direction and an operating lever 83. One of the pulleys 81 and 82 such as, for example, the left pulley 81 is rotatably supported by the hip pad member 3a (not illustrated). Moreover, the operating lever 83 is rotatably supported by the hip pad member 3a so as to be swingable with a shaft 83b at one end thereof as a fulcrum. In addition, the other pulley 82 is rotatably supported by the middle part of the operating lever 83.

Thus, the distance between the pulleys 81 and 82 increases or decreases by swinging the operating lever 83.

Moreover, the wire 31 is wrapped around the pulleys 81 and 82 as illustrated. Additionally, the wire 31 led out from the lower part of the left pulley 81 is extended toward the right leg link mechanism 10R. Furthermore, the wire 31 led out from the lower part of the right pulley 82 is extended toward the left leg link mechanism 10L.

In addition, the operating lever 83 has a ratchet mechanism not illustrated. Thereby, the operating lever 83 is made swingable when a button 83a at the upper end of the operating lever 83 is pressed. Furthermore, the swing position of the operating lever 83 is maintained by releasing the pressing operation of the button 83a in a desired swing position of the operating lever 83.

The provision of the path length control mechanism 80 enables an appropriate change in the path length of the wire 31 in a position of the back part of the hip pad member 3a. Therefore, for example, when the user P sits in a chair or the like or squats, the bending degree of the legs at which the elastic forces of the spring members 20L and 20R start to be generated is able to be decreased by operating the operating lever 83 so as to increase the path length of the wire 31 (for example, operating the operating lever 83 as indicated by a two-dot chain line in FIG. 15).

Moreover, the path length control mechanism 90 illustrated in FIG. 16 has a nut 81 and a bolt 92 screwed into the nut 91. Through-holes are bored in the nut 91 and the bolt 92 in the axis part thereof. Furthermore, the wire 31 is inserted into the through-holes. Moreover, in the path length control mechanism 90 illustrated in FIG. 16, the outer tube 32 is divided into two parts. Furthermore, the end of an outer tube 32a as one part (the outer tube on the left side in the illustrated example) is connected to the end of the nut 91. An outer tube 32b as the other part (the outer tube on the right side in the illustrated example) is connected to the head of the bolt 92.

In the path length control mechanism 90 having the above configuration, a rotation of the bolt 92 changes the protrusion amount of the bolt 92 from the nut 91. This enables a change in the path length of the wire 31 (the path length of the body attachment member 2 in a position on the back side of the hip pad member 3a of the body attachment member 2). Therefore, for example, when the user P sits in a chair or the like or squats, the rotation of the bolt 92 in such a way as to increase the path length of the wire 31 enables the bending degree of the legs at which the elastic forces of the spring members 20L and 20R start to be generated to be further decreased.

Figure 17:
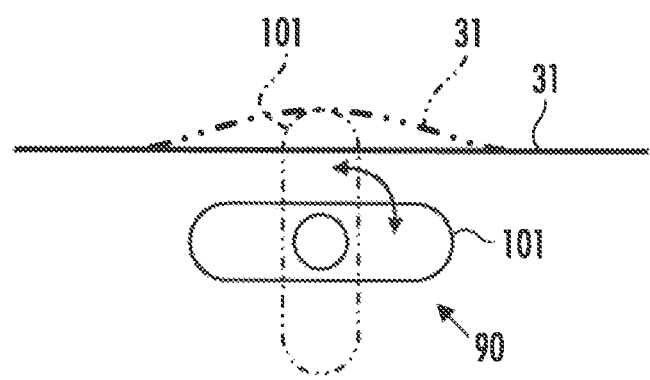
FIG. 17 is a diagram illustrating a third example of the path length control mechanism.

Moreover, as the path length control mechanism, the mechanism having the configuration as illustrated in FIG. 17 may be employed. This path length control mechanism 100 changes the path length of the wire 31 by engaging a rotatable lever 101 with the wire 31 in the middle of the disposition path of the wire 31.

In this case, the lever 101 is installed in one or both of the leg link mechanisms 10L and 10R so as to be rotatable between the rotational position indicated by a solid line and the rotational position indicated by a two-dot chain line illustrated in FIG. 17. Furthermore, the lever 101 does not engage with the wire 31 in the rotational position indicated by the solid line. If the lever 101 is rotated up to the rotational position indicated by the two-dot chain line, however, the lever 101 engages with the wire 31 in such a way as to cause the wire 31 to swell in the traverse direction. This enables an increase in the path length of the wire 31.

In addition, the path length control mechanism may be implemented by a wide variety of mechanisms such as a mechanism with a sprocket and a chain.

Moreover, also in the motion support device 1C according to the third embodiment or the motion support device 1D according to the fourth embodiment, a path length control mechanism similar to the path length control mechanism 80, 90, 100 or the like may be interposed as a first bending degree control mechanism in the middle of the disposition path of each of the wires 61L and 61R. This enables a further decrease in the bending degree of the legs at which the elastic force of the spring member 50 starts to be generated in the case of bending both legs of the user P also in the motion support devices 1C and 1D.

Moreover, for example, if the entire spring member 50 is movable in a relatively long distance in the motion support device 1C according to the third embodiment or the motion support device 1D according to the fourth embodiment, the path length control mechanism may be provided only one of the wires 61L and 61R.

Furthermore, the path length control mechanism may include an actuator such as an electric motor which generates a driving force for changing the path length of the wire (flexible long member). For example, the path length control mechanism 80 may include an electric motor for swingably driving the operating lever 83, the path length control mechanism 90 may include an electric motor for rotationally driving the bolt 92, or the path length control mechanism 100 may include an electric motor for rotationally driving the lever 101.

In this manner, even in the case where the path length control mechanism includes the actuator such as the electric motor, the driving force for changing the path length of the wire (flexible long member) may be relatively small. Therefore, a compact and lightweight electric motor or the like is able to be used as an actuator. Furthermore, a compact battery is able to be used as a power supply therefor. Therefore, even in the case of including the aforementioned actuator, a limb motion support device with a lightweight and simple configuration can be achieved.

Furthermore, in the case of bending both legs of the user P, the control mechanism (first bending degree control mechanism) for use in enabling an appropriate change in the bending degree of the legs at which the elastic force of the spring member starts to be generated is not limited to the path length control mechanism as described above. For example, if the spring member is configured so as to be able to change the natural length thereof, the bending degrees of the legs at which the elastic force of the spring member starts to be generated are able to be changed by adjusting the natural length of the spring member. For example, if the spring member is formed of an air spring, the natural length of the spring member is able to be changed by adjusting the amount of air filling the spring member.

Moreover, in the first and second embodiments, there has been described the motion support device in which the outer tube 32 is disposed on the back side of the body of the user P. In the third and fourth embodiments, there has been described the motion support device in which the spring member 50 and members (the guide tube 51 and the like) accompanying the spring member 50 are disposed on the back side of the body of the user P.

The outer tube 32 in the first and second embodiments, however, may be disposed on the front side of the body of the user P. Similarly, the spring member 50 and the like in the third and fourth embodiments may be disposed on the front side of the body of the user P.

Thus, even in a state where the user P is sitting, the motion support device 1A, 1B, 1C, or 1D is able to be easily attached to the user P.

Furthermore, in the first and second embodiments, there has been described the motion support device in which each leg link mechanism 10 includes the first pulley 34 and the second pulley 35, each of which is eccentric cam-shaped. Note that, however, one or both of the first pulley 34 and the second pulley 35 may be circular-shaped.

Moreover, one of the first pulley 34 and the second pulley 35 may be omitted. Even in the case of omitting the first pulley 34, an assisting force generated by the elastic force of the spring member 20 or 40 is able to be applied to the user P when both legs of the user P are bent at the respective knees. Furthermore, even in the case of omitting the second pulley 35, the assisting force generated by the elastic force of the spring member 20 or 40 is able to be applied to the user P when both legs of the user P are bent at the respective hip joints. Therefore, when the user P sits in a chair or the like or squats, the assisting force is able to be applied to the user P.

When the user P sits in a chair or the like or squats, the bending degrees of the legs at which the elastic force of the spring member 20 or 40 starts to be substantially generated in the case where both of the first pulley 34 and the second pulley 35 are provided is able to be made smaller than the bending degrees of the legs in the case where one of the first pulley 34 and the second pulley 35 is omitted.

Figure 18:
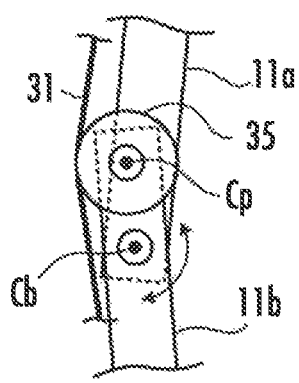
FIG. 18 is a diagram illustrating another example of a pulley installation structure provided in a motion transmission mechanism of the embodiments.

Moreover, in the first and second embodiments, for example, as illustrated in FIG. 18, the second pulley 35 may be circular-shaped. Furthermore, the second pulley 35 may be rotatably supported by one of the first link 11a and the second link 11b such as, for example, the second link 11b in a state where the rotation axis Cp of the second pulley 35 is offset from the swing axis Cb (the rotation axis of a relative rotation between the first link 11a and the second link 11b of each leg link mechanism 10). In this example, the first link 11a and the second link 11b of each leg link mechanism 10 correspond to the two link members of the present invention.

In this arrangement, a frictional force generated between the wire 31 and the second pulley 35 during the bending motion of the legs of the user P can be made significantly smaller than the frictional force in the first or second embodiment. Therefore, the present invention is able to reduce the energy loss that occurs when the motion support device 1A or 1B generates the assisting force and to generate the assisting force efficiently.

In addition, the same aspect as the above may be employed regarding not only the second pulley 35, but also the first pulley 34. Specifically, the first pulley 34 may be circular-shaped. Furthermore, the first pulley 34 may be rotatably supported by one of the mounting plate 4 and the first link 11a (for example, the first link 11a) in a state where the rotation axis of the first pulley 34 is offset from the swing axis Ca (the rotation axis of a relative rotation between the mounting plate 4 and the first link 11a related to each leg link mechanism 10). In this case, the mounting plate 4 and the first link 11a related to each leg link mechanism 10 correspond to the two link members of the present invention.

Furthermore, for example, in the third or fourth embodiment, the present invention may be configured in such a way that a pulley 34 arranged as illustrated in FIG. 18 is provided, instead of the pulley 64 of each leg link mechanism 10 and that each wire 61 is wrapped around the pulley 34.

Moreover, in the third or fourth embodiment, for example, a pulley may be provided in the hip joint portion (a portion bending in conjunction with the bending of the leg of the user P at the hip joint) of each leg link mechanism 10, in the same manner as the first pulley 34 of the first or second embodiment. In addition, each wire 61 may be disposed via the outer periphery of the pulley.

In this arrangement, the path length of each wire 61 is able to be changed in response to the bending at the hip joint in addition to the bending at the knee of the leg of the user P. Therefore, when the user P sits in a chair or the like or squats, the bending degrees of the legs at which the elastic force of the spring member 50 starts to be generated (consequently, the assisting force starts to be generated) is able to be made smaller than that of the third or fourth embodiment. On the other hand, during walking of the user P, it is possible to prevent the elastic force of the spring member 50 from being generated (consequently, prevent the assisting force for the leg of the user P from being generated), similarly to the third or fourth embodiment.

In this case, the pulley in the hip joint portion of each leg link mechanism 10 is not limited to the eccentric cam-shaped pulley, but may be a circular-shaped pulley. In addition, if the pulley is a circular-shaped pulley, the rotation axis may be offset from the swing axis Ca (the rotation axis of a relative rotation between the mounting plate 4 and the first link 11a related to each leg link mechanism 10).

Moreover, while the wire 31 or 61 has been used as a flexible long member in each embodiment, the flexible long member in the present invention is not limited to the wire, but may be a belt, a chain, or the like or may be one having a structure in which these plural types of flexible long members are joined with each other.

Moreover, although there has been described a device which supports the bending and stretching motion of the right and left legs of the user P in each embodiment, the limb motion support device of the present invention may be configured to support a bending and stretching motion of the right and left arms of the user P.

What is claimed is:

1. A limb motion support device comprising:
a pair of braces adapted to be attached to the right and left limbs of a user, respectively;
one or more spring members that generate elastic forces for assisting a bending and stretching motion of the right and left limbs by an elastic deformation, and are shared between the right and left limbs; and
a motion transmission mechanism that transmits a motion between the pair of braces and the one or more spring members so as to elastically deform the one or more spring members by transmitting movements of the pair of braces associated with the bending and stretching motion of the right and left limbs to the one or more spring members,
wherein:
the motion transmission mechanism is configured not to transmit the movements of the pair of braces to the one or more spring members in a state where bending degrees of the right and left limbs are smaller than a predetermined first bending degree, in a case where both of the right and left limbs equipped with the pair of braces are bent from a stretched state, but configured to transmit the movements of the pair of braces to the one or more spring members after increasing the bending degrees of the right and left limbs to a bending degree larger than the predetermined first bending degree;
the right and left limbs are right and left legs of the user; and
in a case where one of the right and left legs equipped with the pair of braces is stretched and the other leg is bent, the motion transmission mechanism is configured not to transmit the movements of the pair of braces to the one or more spring members in a state where a bending degree of the other leg is smaller than a predetermined second bending degree, which is larger than the predetermined first bending degree.

2. A limb motion support device comprising:
a pair of braces adapted to be attached to the right and left limbs of a user, respectively;
one or more spring members that generate elastic forces for assisting a bending and stretching motion of the right and left limbs by an elastic deformation, and are shared between the right and left limbs; and
a motion transmission mechanism that transmits a motion between the pair of braces and the one or more spring members so as to elastically deform the one or more spring members by transmitting movements of the pair of braces associated with the bending and stretching motion of the right and left limbs to the one or more spring members,
wherein:
the motion transmission mechanism is configured not to transmit the movements of the pair of braces to the one or more spring members in a state where bending degrees of the right and left limbs are smaller than a predetermined first bending degree, in a case where both of the right and left limbs equipped with the pair of braces are bent from a stretched state, but configured to transmit the movements of the pair of braces to the one or more spring members after increasing the bending degrees of the right and left limbs to a bending degree larger than the predetermined first bending degree;
a pair of flexible long members are provided as constituent elements of the motion transmission mechanism;
one of the pair of flexible long members is disposed to be engaged with the brace adapted to be attached to the left limb in such a way that at least a part of one of the flexible long members runs due to a change in a path length of the flexible long member at least in a part of a section between both ends of the one flexible long member according to a change in the bending degree of the left limb;
the other of the pair of flexible long members is disposed to be engaged with the brace adapted to be attached to the right limb in such a way that at least a part of the other flexible long member runs due to a change in the path length of the flexible long member at least in a part of a section between both ends of the other flexible long member according to a change in the bending degree of the right limb; and
the motion transmission mechanism is configured to run at least a part of each of the pair of flexible long members according to a change in the bending degrees of the right and left limbs so that a running motion of each of the flexible long members is not transmitted to the one or more spring members, in a state where the bending degrees of the right and left limbs are smaller than the predetermined first bending degree, and configured to cause an elastic deformation of the one or more spring members by running at least a part of each of the pair of flexible long members so as to apply a pulling force or a compressive force to the one or more spring members via a pair of fifth members from the pair of flexible long members according to an increase in the bending degrees of the right and left limbs with the pair of fifth members each connected to one end of each of the pair of flexible long members bound to both ends of the one or more spring members in a state where the bending degrees of the right and left limbs are larger than the predetermined first bending degree.

3. The limb motion support device according to claim 2, wherein:
one of the flexible long members is disposed in such a way as to extend from one end side of the one or more spring members toward the other end side thereof and the other flexible long member is disposed in such a way as to extend from the other end side of the one or more spring members toward one end side thereof; and
the motion transmission mechanism is configured to run each of the pair of flexible long members so that the fifth member connected to the one of the flexible long members comes close from an opposite side of the one end of the one or more spring members to the other end thereof with an increase in the bending degree of the left limb and also the fifth member connected to the other flexible long member comes close from the opposite side of the other end of the one or more spring members to the one end thereof with an increase in the bending degree of the right limb in a state where the bending degrees of the right and left limbs are smaller than the predetermined first bending degree, and configured to cause an elastic deformation of the one or more spring members in a compression direction by running the pair of flexible long members in such a way as to decrease a distance between the pair of fifth members with an increase in the bending degrees of the right and left limbs with each of the pair of fifth members bound to both ends of the one or more spring members due to an engagement of each of the fifth members with both ends of the one or more spring members in a state where the bending degrees of the right and left limbs are larger than the predetermined first bending degree.

4. The limb motion support device according to claim 3, wherein the one or more spring members is movably arranged between a position in which one end of the one or more spring members engages with one of the pair of fifth members and a position in which the other end of the one or more spring members engages with the other of the pair of fifth members.

5. The limb motion support device according to claim 2, wherein:
the right and left limbs are right and left legs of the user; and
each of the pair of flexible long members is disposed in such a way that the path length increases according to an increase in the bending degree of each leg at a knee of the user.

6. The limb motion support device according to claim 5, wherein each of the pair of flexible long members is disposed in such a way that the path length increases according to an increase in the bending degree of each leg at the knee of the user and an increase in the bending degree of the leg at the hip joint.

7. The limb motion support device according to claim 2, wherein each of the pair of braces is provided with a circular or eccentric cam-shaped pulley, which rotates in response to the bending of the limb equipped with each brace, and one of the flexible long members is disposed via an outer periphery of the pulley installed in the brace adapted to be attached to the left limb out of the right and left limbs and the other flexible long member is disposed via the outer periphery of the pulley installed in the brace attached to the right limb out of the right and left limbs.

8. The limb motion support device according to claim 2, wherein:
each of the pair of braces has at least two link members connected so as to relatively rotate in response to the bending of the limb equipped with the brace and a circular pulley rotatably supported by one of the two link members around a rotation axis in a position offset from the rotation axis of the relative rotation of the two link members; and
each of the pair of flexible long members is disposed via an outer periphery of the pulley of each of the pair of braces.

9. The limb motion support device according to claim 2, wherein the one or more spring members is arranged so as to expand and contract in a right-and-left direction on a back side or a front side of a body of the user.

10. The limb motion support device according to claim 2, further comprising a first bending degree control mechanism which changes the predetermined first bending degree.

11. The limb motion support device according to claim 10, wherein the first bending degree control mechanism includes a mechanism which changes the path length in a part of a section of at least one of the pair of flexible long members.

12. The limb motion support device according to claim 11, wherein the first bending degree control mechanism includes an actuator that generates a driving force for changing the path length.

* * * * *